(12) United States Patent
Ikemoto et al.

(10) Patent No.: US 6,372,804 B1
(45) Date of Patent: Apr. 16, 2002

(54) NOXIOUS-INSECT REPELLENT

(75) Inventors: Takeshi Ikemoto; Hiroyuki Nishio; Hiroko Nakatsugawa, all of Odawara (JP)

(73) Assignee: Kanebo, Ltd., Tokyo (JP)

( * ) Notice: Subject to any disclaimer, the term of this patent is extended or adjusted under 35 U.S.C. 154(b) by 0 days.

(21) Appl. No.: 09/492,351

(22) Filed: Jan. 27, 2000

Related U.S. Application Data

(62) Division of application No. 08/635,926, filed as application No. PCT/JP94/00885 on Jun. 1, 1994, now Pat. No. 6,130, 255.

(30) Foreign Application Priority Data

| Sep. 2, 1991 | (JP) | 3-250533 |
| Sep. 18, 1991 | (JP) | 3-268219 |
| Nov. 20, 1991 | (JP) | 3-332572 |
| Dec. 14, 1991 | (JP) | 3-351875 |
| Dec. 14, 1991 | (JP) | 3-351876 |
| Dec. 19, 1991 | (JP) | 3-355233 |
| Feb. 3, 1992 | (JP) | 4-48088 |
| Oct. 22, 1993 | (JP) | 5-287569 |
| Oct. 29, 1993 | (JP) | 5-294763 |
| Nov. 11, 1993 | (JP) | 5-307310 |
| Nov. 16, 1993 | (JP) | 5-311181 |
| Jun. 1, 1994 | (WO) | PCT/JP94/00885 |

(51) Int. Cl.[7] .................. A01N 31/06; A01N 31/04; A01N 25/00; A01N 25/08; A01N 25/34
(52) U.S. Cl. .................. 514/729; 424/402; 424/403; 424/409; 424/411; 424/414; 424/443; 424/400; 424/DIG. 10; 514/919
(58) Field of Search .................. 514/729, 919; 424/400, 402, 403, 409, 411, 414, 443, DIG. 10

(56) References Cited

U.S. PATENT DOCUMENTS

| 2,407,205 A | * | 9/1946 | Wilkes | 514/738 |
| 4,845,131 A | * | 7/1989 | Behrenz et al. | 514/729 |
| 5,017,377 A | * | 5/1991 | Sikinami et al. | 514/729 |
| 5,648,398 A | * | 7/1997 | Beldock et al. | 514/703 |
| 6,183,767 B1 | * | 2/2001 | Bessette et al. | 424/406 |

FOREIGN PATENT DOCUMENTS

| JP | 5-213802 | * | 8/1993 |

* cited by examiner

*Primary Examiner*—John Pak
(74) *Attorney, Agent, or Firm*—Flynn, Thiel, Boutell & Tanis, P.C.

(57) ABSTRACT

Disclosed is a method of repelling noxious insects comprising the step of exposing said noxious insects to a composition containing from 0.1 to 90 wt. %, based on the total weight of the composition, of at least one of 2-(1-hydroxyalkyl)cycloalkanols represented by the following formulae (9) and (10):

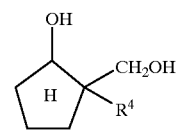

(9)

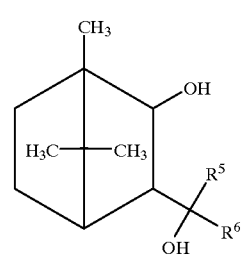

(10)

wherein $R^4$ is a straight-chain or branched, saturated or unsaturated, hydrocarbon radical having 1–8 carbon atoms and $R^5$ and $R^6$ are hydrogens or lower alkyl groups having at most 3 carbon atoms and the sum of the carbon atoms of $R^5$ and $R^6$ is 0–3.

10 Claims, No Drawings

NOXIOUS-INSECT REPELLENT

This is a division of U.S. Ser. No. 08/635 926, filed Nov. 6, 1996 now U.S. Pat. No. 6,130,255 which is a 371 of PCT/JP94/00885, filed on Jun. 1, 1994.

TECHNICAL FIELD

The present invention relates to noxious-insect repellents comprising a compound which is substantially odorless and has an extremely excellent noxious-insect repelling effect and durability.

BACKGROUND ART

As a noxious-insect repellent for protecting bodies from noxious-insects such as mosquitoes, flies and the like, a preparation applied to the skin which contains N,N-diethyltoluamide has so far been extensively used. Additionally, it has been known that p-menthane-3,8-diol and 8-hydroxy-p-menthan-3-one have a strong insect-repelling effect (Japanese Patent Application Kokai Nos. 60-199,804 and 5-173,104) and that 2-ethyl-1,3-hexanediol and 2-(1-hydroxyethyl)-cyclohexanol also have a similar repelling effect (U.S. Pat. No. 2,407,205). However, problems have been posed such that N,N-diethyltoluamide has a peculiar offensive odor and p-menthane-3,8-diol, 8-hydroxy-p-menthan-3-one, 2-ethyl-1,3-hexanediol or 2-(1-hydroxyethyl)-cyclohexanol lacks durability. Therefore, development of novel noxious-insect repellents has been expected.

The present invention has been accomplished under these circumstances. The object of the present invention is to provide noxious-insect repellents which have no peculiar offensive odor and exhibit an excellent noxious-insect repelling effect and durability.

DISCLOSURE OF INVENTION

We, the inventors, as a result of assiduous studies conducted in order to achieve the above object, have succeeded in synthesizing substantially odorless compounds having an excellent noxious-insect repelling effect and durability, and thus accomplished the present invention.

Namely, the first embodiment of the present invention is a noxious-insect repellent which contains 0.1–90% by weight, based on the total weight, of at least one of 2-(1-hydroxy-alkyl)-cycloalkanols represented by the following general structural formula (1):

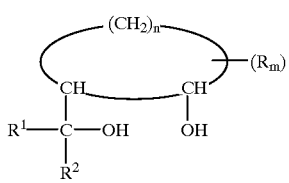

(1)

wherein n is an integer of 3–10, $R^1$ is hydrogen or a straight-chain saturated hydrocarbon radical having 1–6 carbon atoms; $R^2$ is hydrogen or methyl group; $R_m$ represents m of the same or different, straight-chain or branched, saturated or unsaturated, hydrocarbon radicals R which, as a substituent group, can be bonded to carbocyclic atoms; m is an integer of 0–8, provided that m should be at least 1 when either one of $R^1$ or $R^2$ is an alkyl group and m should be at least 2 when both the $R^1$ and $R^2$ are alkyl groups; the sum of the carbon atoms of $R_m$ does not exceed 8; and, further, when n is 4, R may by an isopropylidene group which intramolecularly bridges between the third and sixth carbocyclic atoms.

Among the above 2-(1-hydroxyalkyl)-cycloalkanols, preferred are 2-(1-hydroxyisopropyl)-5-methyl-cyclohexanol derivatives represented by the following general structural formula (2):

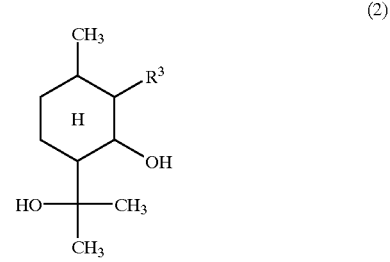

(2)

wherein $R^3$ is a straight-chain or branched, saturated or unsaturated, hydrocarbon radical having 1–8 carbon atoms; 2-(1-hydroxyisopropyl)-5,6-dimethyl-cyclohexanol represented by the following chemical structural formula (3):

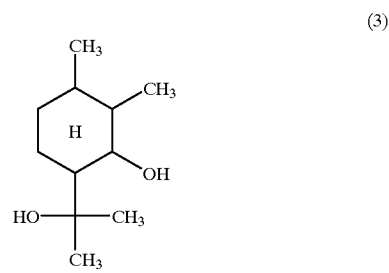

(3)

2-(1-hydroxyisopropyl)-5-methyl-6-methylene-cyclohexanol represented by the following chemical structural formula (4):

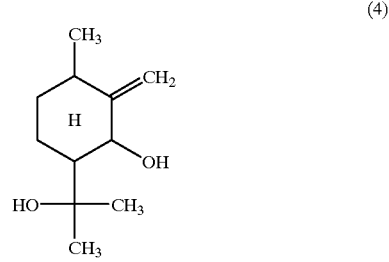

(4)

and, 2-(1-hydroxyalkyl)-cycloalkanols represented by the following general structural formula (5):

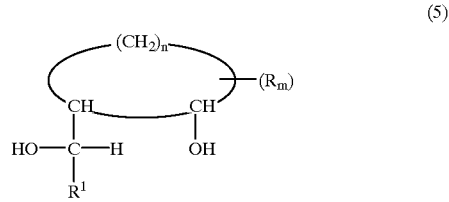

(5)

wherein n, m, $R_m$ and $R^1$ are the same as above; particularly, 2-(hydroxymethyl)-cycloalkanols represented by the following general structural formula (6):

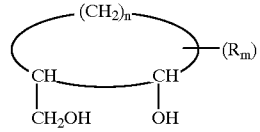

(6)

wherein n, m and $R_m$ are the same as above; and inter alia 2-(hydroxymethyl)-3-methyl-6-isopropyl-cyclohexanol represented by the following chemical structural formula (7):

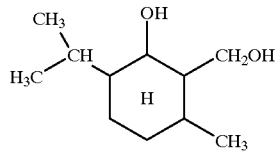

(7)

Furthermore, among the 2-(1-hydroxyalkyl)-cycloalkanols represented by the general structural formula (5), particularly preferred are 2-(1-hydroxymethyl)-cyclohexanol derivatives represented by the following general structural formula (8):

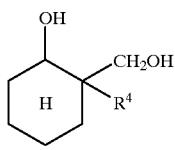

(8)

wherein $R^4$ is a straight-chain or branched, saturated or unsaturated, hydrocarbon radical having 1–8 carbon atoms; and 2-(1-hydroxymethyl)-cyclopentanol derivatives represented by the following general structural formula (9):

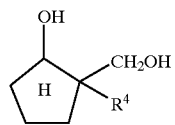

(9)

wherein $R^4$ is the same as above.

Furthermore, preferred examples of the present invention include 3-(1-hydroxyalkyl)-borneol derivatives represented by the following general structural formula (10) which, in the 2-(1-hydroxyalkyl)-cycloalkanols represented by the general structural formula (1), is specified by defining n as 4 to form a 6-membered carbocycle and $R_m$ as an isopropylidene group intramolecularly bridging between the third and sixth carbocyclic atoms:

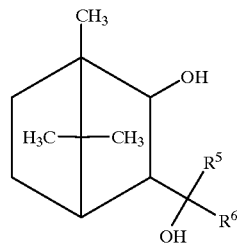

(10)

wherein $R^5$ and $R^6$ are hydrogens or lower alkyl groups having at most 3 carbon atoms and the sum of the carbon atoms of $R^5$ and $R^6$ is 0–3.

The most preferable noxious-insect repellents of the above first embodiment of the present invention contain 0.1–90%, preferably 3–20%, by weight, based on the total weight, of at least one compound selected from the group consisting of the 2-(1-hydroxyalkyl)-cycloalkanols represented by the formulae (2), (3), (4), (5), (6), (7), (8), (9) and (10).

The second embodiment of the present invention is a noxious-insect repellent which contains 0.1–90% by weight, based on the total weight, of at least one of 2-(1-hydroxyalkyl)-cycloalkanones represented by the following general structural formula (11):

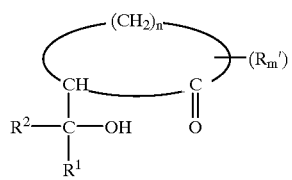

(11)

wherein n, $R^1$ and $R^2$ are the same as above; $R_m'$ represents m' of the same or different, straight-chain or branched, saturated or unsaturated, hydrocarbon radicals R which, as a substituent group, can be bonded to carbocyclic atoms; m' is an integer of 0–8, provided that m' should be at least 2 when n is at least 4 and both the $R^1$ and $R^2$ are alkyl groups; the sum of the carbon atoms of $R_m'$ does not exceed 12; and, further, when n is 4, R may be an isopropylidine group which intramolecularly bridges between the third and sixth carbocyclic atoms.

Among the above compounds represented by the formula (11) that are contained in the noxious-insect repellents, preferably used are 2-(1-hydroxyisopropyl)-cycloalkanone derivatives represented by the following general structural formula (12):

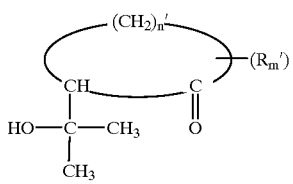

(12)

wherein n' is an integer of 3 or 4; when n' is 3, m' is at least 1; and when n' is 4, m' is at least 2.

Among the 2-(1-hydroxyisopropyl)-cycloalkanone derivatives represented by the above formula (12), further particularly preferred is 2-(1-hydroxyisopropyl)-5-methyl-cyclopentanone represented by the following chemical formula (13) and 2-(1-hydroxyisopropyl)-5-methyl-cyclohexanone derivatives represented by the following chemical formula (14):

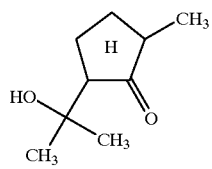
(13)

and

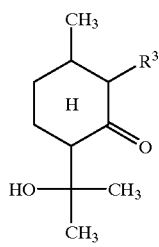
(14)

wherein $R^3$ is the same as above.

Among the 2-(1-hydroxyalkyl)-cycloalkanones represented by the above general structural formula (11), further preferred are 2-(1-hydroxyalkyl)-cycloalkanones represented by the following general structural formula (15) and 2-(hydroxymethyl)-cycloalkanones represented by the following general structural formula (16), particularly, 2-(1-hydroxymethyl)-3-methyl-6-isopropyl-cyclohexanone represented by the following chemical structural formula (17):

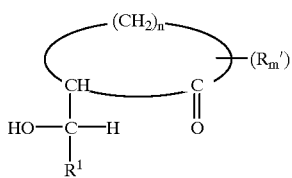
(15)

wherein n, m', $R_m'$ and $R^1$ are the same as above;

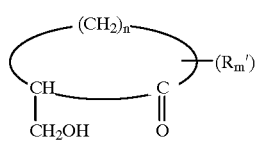
(16)

wherein n, m' and $R_m'$ are the same as above; and

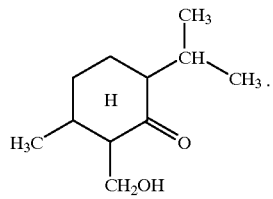
(17)

The preferred examples of the present invention include 3-(1-hydroxyalkyl)-camphor derivatives represented by the following general structural formula (18) which, in the 2-(1-hydroxyalkyl)-cycloalkanones represented by the foregoing general formula (11), is specified by defining n as 4 to form a 6-membered carbocycle and $R_m'$ as an isopropylidene group intramolecularly bridging between the third and sixth carbocyclic atoms:

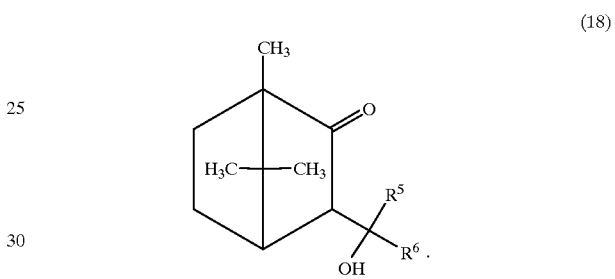
(18)

wherein $R^5$ and $R^6$ are the same as above.

The most preferred second embodiment of the present invention are noxious-insect repellents containing 0.1–90%, preferably 3–20%, by weight, based on the total weight, of at least one compound selected from the group consisting of the compounds represented by the above chemical structural formulae (12), (13), (14), (15), (16), (17) and (18).

The construction of the present invention will be explained in detail hereinafter.

The 2-(1-hydroxyisopropyl)-5,6-dimethyl-cyclohexanol shown by the chemical structural formula (3) which falls in the scope of the above general structural formulae (1) and (2), that is, p-menthane-2-methyl-3,8-diol (referred to as "MMD" hereinafter), can be obtained by admixing 2,3,7-trimethyl-6-octenal (referred to as "TO" hereinafter) with an aqueous solution of an acid, such as sulfuric acid or the like, while stirring. Alternatively, the 2-(1-hydroxyisopropyl)-5-methyl-6-methylene-cyclohexanol shown by the chemical structural formula (4), that is, p-menthane-2-methylene-3,8-diol (referred to as "MMED" hereinafter), can be obtained by admixing 3,7-dimethyl-2-methylene-6-octenal (referred to as "DMO" hereinafter) with an aqueous solution of an acid such as sulfuric acid or the like, while stirring.

It has been known that both the 2,3,7-trimethyl-6-octenal (TO) and 3,7-dimethyl-2-methylene-6-octenal (DMO) are compounds which can easily be obtained from citronellal (U.S. Pat. No. 3,463,818). Both the MMD and MMED obtained by the above synthesizing process are colorless, transparent, oily substances having substantially no odor.

The 2-(1-hydroxyisopropyl)-5-methyl-cyclohexanol derivatives shown by the general structural formula (2), which are used in the present invention, i.e., p-menthane-2-alkyl-3,8-diol derivatives, can be obtained by admixing 2-alkyl-3,7-dimethyl-6-octenal with an aqueous solution of an acid such as sulfuric acid or the like, while stirring. It has been known that the 2-alkyl-3,7-dimethyl-6-octenal, which is a starting material for producing the p-menthane-2-alkyl-3,8-diol, can easily be obtained from citronellal (Summary Report of Lectures, presented in 35th Symposium on Perfume, Terpene & Essential Oil Chemistry, p. 62, 1991).

The p-menthane-2-alkyl-3,8-diol derivatives obtained by the above synthesizing process are colorless, transparent, oily substances having substantially no odor.

The above p-menthane-2-alkyl-3,8-diol derivatives include, for example:
p-menthane-2-ethyl-3,8-diol,
p-menthane-2-propyl-3,8-diol,
p-menthane-2-butyl-3,8-diol,
p-menthane-2-pentyl-3,8-diol,
p-menthane-2-hexyl-3,8-diol,
p-menthane-2-isopropyl-3,8-diol,
p-menthane-2-(3-methylbutyl)-3,8-diol,
p-menthane-2-(2-propenyl)-3,8-diol,
p-menthane-2-(3-butenyl)-3,8-diol,
p-menthane-2-(cis-3-hexenyl)-3,8-diol,
p-menthane-2-octyl-3,8-diol,
and the like.

The 2-hydroxymethyl-2-alkyl-cyclohexanols shown by the general formula (8) falling in the scope of the 2-(1-hydroxyalkyl)-cycloalkanol derivatives shown by the above general structural formula (1), which are applied in the present invention, can be produced by a manufacturing process wherein 2-ethoxycarbonyl cyclohexanone obtained from cyclohexanone by a conventional process is reacted with an alkylbromide to provide 2-ethoxycarbonyl-2-alkyl-cyclohexanone which is then reduced by using lithium borohydride as a reducing agent (Organic Synthesis, Vol. 47, p. 20, 1967).

The 2-hydroxymethyl-cyclohexanol derivatives obtained by the above synthesizing process are colorless, transparent, oily substances having substantially no odor.

The 2-hydroxymethyl-cyclohexanol derivatives to be employed in the present invention include compounds derived by adding a saturated straight-chain or branched alkyl group having 1–12 carbon atoms to the second carbocyclic atom of a 2-hydroxymethyl-cyclohexanol, such as:
2-hydroxymethyl-2-methyl-cyclohexanol,
2-hydroxymethyl-2-ethyl-cyclohexanol,
2-hydroxymethyl-2-propyl-cyclohexanol,
2-hydroxymethyl-2-isopropyl-cyclohexanol,
2-hydroxymethyl-2-butyl-cyclohexanol,
2-hydroxymethyl-2-hexyl-cyclohexanol,
2-hydroxymethyl-2-octyl-cyclohexanol,
2-hydroxymethyl-2-decyl-cyclohexanol,
2-hydroxymethyl-2-dodecyl-cyclohexanol,
and the like.

The substituent alkyl group at the second carbon atom is preferred to have about 1–8 carbon atoms in view of the volatility of the compounds.

The 2-hydroxymethyl-2-alkyl-cyclopentanols shown by the general formula (9) falling in the scope of the 2-(1-hydroxyalkyl)-cyclopentanol derivatives shown by the above general structural formula (1), which are applied in the present invention, can be produced by a manufacturing process wherein 2-ethoxycarbonyl-cyclopentanone obtained from cyclopentanone by a conventional process is reacted with an alkylbromide to provide 2-ethoxycarbonyl-2-alkyl-cyclopentanone which is then reduced by using lithium borohydride as a reducing agent (Organic Synthesis, Vol. 47, p. 20, 1967).

It has been reported that 2-hydroxy-2-nonyl-cyclopentanol, as an intermediate of synthesis, was isolated by the above process. However, there has never been disclosed that this compound has a noxious-insect repelling effect (Chem. Pharm. Bull., p. 3047, Vol. 29, 1981).

The 2-hydroxymethyl-cyclopentanol derivatives obtained by the above synthesizing process are colorless, transparent, oily substances having substantially no odor.

The 2-hydroxymethyl-cyclopentanol derivatives of the formula (9) to be employed in the present invention include compounds derived by adding a saturated straight-chain or branched alkyl group having 1–12 carbon atoms to the second carbocyclic atom of a 2-hydroxymethyl-cyclopentanol, such as:
2-hydroxymethyl-2-methyl-cyclopentanol,
2-hydroxymethyl-2-ethyl-cyclopentanol,
2-hydroxymethyl-2-propyl-cyclopentanol,
2-hydroxymethyl-2-isopropyl-cyclopentanol,
2-hydroxymethyl-2-butyl-cyclopentanol,
2-hydroxymethyl-2-hexyl-cyclopentanol,
2-hydroxymethyl-2-octyl-cyclopentanol,
2-hydroxymethyl-2-decyl-cyclopentanol,
2-hydroxymethyl-2-dodecyl-cyclopentanol,
and the like.

The substituent alkyl group at the second carbocyclic atom is preferred to have about 1–8 carbon atoms in view of the volatility of the compounds.

The 2-hydroxymethyl-3-methyl-6-isopropyl-cyclohexanol, that is, 2-hydroxymethyl-menthol (referred to as "HMMO" hereinafter) shown by the chemical formula (7), which is applied in the present invention, can be produced by a manufacturing process wherein 2-ethoxycarbonyl-menthone is obtained from menthone and diethyl carbonate, and then reduced.

The HMMO obtained by the above synthesizing process is a colorless, transparent, oily substance having substantially no odor.

The 2-hydroxymethyl-cycloalkanol derivatives shown by the general structural formula (6), which are employed in the present invention, can be produced by reducing, with lithium borohydride, a 2-ethoxycarbonyl cycloalkanone which has been obtained by a conventional process from a cycloalkanone comprising a straight-chain or branched, saturated, substituent hydrocarbon radical having 0–8 total carbon atoms added to a carbocyclic atom thereof (Organic Synthesis, Vol. 47, p. 20, 1967).

The 2-hydroxymethyl-cycloalkanol derivatives obtained by the above synthesizing process is a colorless, transparent, oily substance having substantially no odor.

The 2-hydroxymethyl-cycloalkanol derivatives of the formula (6), which are employed in the present invention, include 2-hydroxymethyl-cycloalkanols comprising a 5–12-membered carbocycle and such compounds further comprising at least one saturated, straight-chain or branched alkyl substituent group having 1–8 total carbon atoms added to the carbocyclic atoms thereof, such as:
2-hydroxymethyl-3-methyl-cyclopentanol,
2-hydroxymethyl-3-ethyl-cyclopentanol,
2-hydroxymethyl-4-propyl-cyclopentanol,
2-hydroxymethyl-4-isopropyl-cyclopentanol,
2-hydroxymethyl-4-methyl-cyclohexanol,
2-hydroxymethyl-5-methyl-cyclohexanol,
2-hydroxymethyl-6-methyl-cyclohexanol,
2-hydroxymethyl-4-ethyl-cyclohexanol, 2-hydroxymethyl-4-(t-butyl)-cyclohexanol,
2-hydroxymethyl-6-(t-butyl)-cyclohexanol,
2-hydroxymethyl-6-(sec-butyl)-cyclohexanol,
2-hydroxymethyl-4-(t-amyl)-cyclohexanol,
2-hydroxymethyl-3,4-dimethyl-cyclohexanol,
2-hydroxymethyl-4,5-dimethyl-cyclohexanol,
2-hydroxymethyl-3,3,5-trimethyl-cyclohexanol,
2-hydroxymethyl-3,5,5-trimethyl-cyclohexanol,
2-hydroxymethyl-cycloheptanol,
2-hydroxymethyl-cyclooctanol,
2-hydroxymethyl-2-ethyl-cyclooctanol,
2-hydroxymethyl-cyclododecanol,
and the like.

The manufacturing process of the 2-(1-hydroxyalkyl)-cycloalkanol derivatives to be employed in the present invention is not specifically limited. The 2-(1-hydroxyalkyl)-cycloalkanol derivatives can be produced by reducing, with a reducing agent such as lithium borohydride, a 2-(1-hydroxyalkyl)-cycloalkanone derivative which has been obtained by a conventional process from an aldehyde and a 2-bromocycloalkanone derivative comprising a straight-chain or branched, saturated substituent hydrocarbon radical having 0–8 total carbon atoms added to the carbocyclic atom thereof (J. Amer. Chem. Soc., Vol. 89, p. 5727, 1967).

The above 2-(1-hydroxyalkyl)-cycloalkanol derivatives include 2-(1-hydroxyalkyl)-cycloalkanols comprising a 5–12-membered carbocycle and these compounds further comprising at least one saturated, straight-chain or branched alkyl substituent group having 0–8 total carbon atoms added to the carbocyclic atoms thereof, such as:

2-(1-hydroxyethyl)-3-methyl-cyclopentanol,
2-(1-hydroxybutyl)-3-ethyl-cyclopentanol,
2-(1-hydroxyethyl)-4-propyl-cyclopentanol,
2-(1-hydroxypropyl)-4-ethyl-cyclopentanol,
2-(1-hydroxyethyl)-4-methyl-cyclohexanol,
2-(1-hydroxyamyl)-5-methyl-cyclohexanol,
2-(1-hydroxyethyl)-6-methyl-cyclohexanol,
2-(1-hydroxybutyl)-4-ethyl-cyclohexanol,
2-(1-hydroxyethyl)-3-methyl-cyclohexanol,
2-(1-hydroxybutyl)-6-methyl-cyclohexanol,
2-(1-hydroxyethyl)-3-methyl-6-isopropyl-cyclohexanol,
2-(1-hydroxybutyl)-4-isopropyl-cyclohexanol,
2-(1-hydroxyethyl)-3,4-dimethyl-cyclohexanol,
2-(1-hydroxyethyl)-4,5-dimethyl-cyclohexanol,
2-(1-hydroxybutyl)-cycloheptanol,
2-(1-hydroxyethyl)-cyclooctanol,
2-(1-hydroxybutyl)-cyclooctanol,
2-(1-hydroxyethyl)-cyclodecanol,
and the like.

The 3-(1-hydroxyalkyl)-borneol derivatives shown by the general formula (10), to be employed in the present invention, can be regarded as a specific structure which, in the 2-(1-hydroxyisoalkyl)-6-methyl-hexanol falling in the scope of the general formula (1), is specified by defining n as 4 and the third and sixth carbocyclic atoms thereof are intramolecularly bridged with an isopropylidene group. These are known compounds. These compounds can be produced by reducing, with a reducing agent such as lithium aluminum hydride, sodium borohydride or the like, 3-(1-hydroxyalkyl)-camphor derivatives which can be prepared according to the process disclosed in J. Org. Chem. Vol. 56, p. 378–387 (1991).

The 3-(1-hydroxyalkyl)-borneol derivatives to be employed in the present invention include:
3-(1-hydroxymethyl)-borneol,
3-(1-hydroxyethyl)-borneol,
3-(1-hydroxypropyl)-borneol,
3-(1-hydroxy-1-methylethyl)-borneol,
3-(1-hydroxybutyl)-borneol,
3-(1-hydroxy-1-methylpropyl)-borneol, and
3-(1-hydroxy-2-methylpropyl)-borneol.

These compounds are substantially odorless.

Among the 2-(1-hydroxyisopropyl)-cycloalkanone derivatives of the general structural formula (12) which fall in the scope of the above general structural formula (11), the 2-(1-hydroxyisopropyl)-5-methyl-cyclopentanone shown by the chemical formula (13) can be produced by oxidizing 2-(1-hydroxyisopropyl)-5-methyl-cyclopentanol, which can be prepared according to the process disclosed in Japanese Patent Application Kokai No. 3–250,533, with a salt or oxide of a metal, such as chromium, manganese, silver or the like, or an organic oxidizing agent (dimethyl sulfoxide or the like). The thus obtained 2-(1-hydroxyisopropyl)-5-methyl-cyclopentanone is a substantially odorless, pale yellow, oily substance.

Similarly, the 8-hydroxy-p-menthan-3-one derivatives shown by the general formula (14) which fall in the scope of the chemical formula (12) can be produced by oxidizing, with a salt or oxide of a metal, such as chromium, manganese, silver or the like, a metal oxide thereof or an organic oxidizing agent (dimethyl sulfoxide or the like), a diol which can be prepared by admixing a 3,7-dimethyl-6-octenal derivative having a substituent hydrocarbon radical at the second carbon atom thereof with an aqueous solution of an acid such as sulfuric acid or the like, while stirring. The thus obtained 8-hydroxy-p-menthan-3-one derivatives are substantially odorless, colorless and transparent, oily substances.

The above 8-hydroxy-p-menthan-3-one derivatives include:
8-hydroxy-2-methyl-p-menthan-3-one,
8-hydroxy-2-methylene-p-menthan-3-one,
8-hydroxy-2-ethyl-p-menthan-3-one,
8-hydroxy-2-propyl-p-menthan-3-one,
8-hydroxy-2-isopropyl-p-menthan-3-one,
8-hydroxy-2-butyl-p-menthan-3-one,
8-hydroxy-2-isobutyl-p-menthan-3-one,
8-hydroxy-2-hexyl-p-menthan-3-one,
8-hydroxy-2-(2-ethylhexyl)-p-menthan-3-one,
8-hydroxy-2-(2-propenyl)-p-menthan-3-one,
8-hydroxy-2-(3-pentenyl)-p-menthan-3-one,
8-hydroxy-2-(2-propenyl)-p-menthan-3-one,
and the like.

The manufacturing process of the 2-hydroxymethyl-cycloalkanone derivatives shown in the general structural formula (16) which are employed in the present invention is not specifically limited. The 2-hydroxymethyl-cycloalkanone derivatives can be produced by reducing selectively an ethoxycarbonyl group of a 2-ethoxycarbonyl cycloalkanone derivative which has been obtained by a conventional process from a cycloalkanone comprising a straight-chain or branched, saturated substituent hydrocarbon radical having 0–12 total carbon atoms added to a carbocyclic atom thereof (Chem. Pharm. Bull., Vol. 29, No. 10, p. 3047, 1981).

The 2-hydroxymethyl-cycloalkanone derivatives of the general structural formula (16) include 2-hydroxymethyl-cycloalkanone comprising a 5–12-membered carbocycle and such compounds further comprising at least one saturated, straight-chain or branched, substituent hydrocarbon radical having 0–12 total carbon atoms added to the carbocyclic atom thereof, such as:

2-hydroxymethyl-3-methyl-cyclopentanone,
2-hydroxymethyl-3-ethyl-cyclopentanone,
2-hydroxymethyl-4-propyl-cyclopentanone,
2-hydroxymethyl-4-isopropyl-cyclopentanone,
2-hydroxymethyl-4-methyl-cyclohexanone,
2-hydroxymethyl-5-methyl-cyclohexanone,
2-hydroxymethyl-6-methyl-cyclohexanone,
2-hydroxymethyl-4-ethyl-cyclohexanone,
2-hydroxymethyl-4-(t-butyl)-cyclohexanone,
2-hydroxymethyl-6-(t-butyl)-cyclohexanone,
2-hydroxymethyl-6-(sec-butyl)-cyclohexanone,
2-hydroxymethyl-4-amyl-cyclohexanone,
2-hydroxymethyl-3,4-dimethyl-cyclohexanone,
2-hydroxymethyl-4,5-dimethyl-cyclohexanone,
2-hydroxymethyl-cycloheptanone,
2-hydroxymethyl-cyclooctanone,
2-hydroxymethyl-2-ethyl-cyclooctanone,
2-hydroxymethyl-cyclododecanone,
and the like.

These compounds are substantially odorless.

The 2-(hydroxymethyl)-3-methyl-6-isopropyl-cyclohexanone shown in the chemical formula (17) which is employed in the present invention, that is, 2-hydroxymethyl-menthone (referred to as "HMMT" hereinafter), can be manufactured by heating, while stirring, menthone and formaldehyde in methanol in the presence of potassium carbonate.

According to the above synthesizing process, the HMMT that is a substantially odorless and colorless, transparent, oily substance is produced.

The manufacturing process of the 2-(1-hydroxyalkyl)-cycloalkanone derivatives shown by the general structural formula (15) which are employed in the present invention, is not specifically limited. The 2-(1-hydroxyalkyl)-cycloalkanone derivatives can be produced according to a conventional process from a 2-bromocycloalkanone derivative having a straight-chain or branched, saturated substituent hydrocarbon radical comprising 0–12 total carbon atoms added to a carbocyclic atom thereof and an aldehyde (J. Amer. Chem. Soc., Vol. 89, p. 5727, 1967).

The 2-(1-hydroxyalkyl)-cycloalkanone derivatives include 2-(1-hydroxyalkyl)-cycloalkanones comprising a 5–12-membered carbocycle and such compounds further comprising at least one saturated, straight-chain or branched, substituent hydrocarbon radical of 0–12 total carbon atoms added to the carbocyclic atom(s) thereof, such as:

2-(1-hydroxyethyl)-3-methyl-cyclopentanone,
2-(1-hydroxybutyl)-3-ethyl-cyclopentanone,
2-(1-hydroxyhexyl)-4-propyl-cyclopentanone,
2-(1-hydroxypropyl)-4-ethyl-cyclopentanone,
2-(1-hydroxyamyl)-4-methyl-cyclohexanone,
2-(1-hydroxyethyl)-3,5-dimethyl-cyclohexanone,
2-(1-hydroxyethyl)-6-methyl-cyclohexanone,
2-(1-hydroxybutyl)-1-ethyl-cyclohexanone,
2-(1-hydroxyethyl)-3-methyl-cyclohexanone,
2-(1-hydroxybutyl)-6-methyl-cyclohexanone,
2-(1-hydroxyethyl)-3-methyl-6-isopropyl-cyclohexanone,
2-(1-hydroxybutyl)-4-isopropyl-cyclohexanone,
2-(1-hydroxyethyl)-3,4-dimethyl-cyclohexanone,
2-(1-hydroxyethyl)-4,5-dimethyl-cyclohexanone,
2-(1-hydroxybutyl)-cycloheptanone,
2-(1-hydroxyethyl)-cyclooctanone,
2-(1-hydroxybutyl)-cyclooctanone,
2-(1-hydroxyethyl)-cyclododecanone,
and the like.

These compounds are substantially odorless.

The 3-(1-hydroxyalkyl)-.camphor derivatives of the general structural formula (18), which are employed in the present invention, can be regarded as a specific structure which, in the 2-(1-hydroxy-isoalkyl)-6-methyl-hexanone shown by the general structural formula (13), is specified by defining n as 4 and the third and sixth carbocyclic atoms thereof are intramolecularly bridged with an isopropylidene group. These are known compounds. These compounds can be manufactured according to the process disclosed in J. Org. Chem., Vol. 56, p. 378–387 (1991). However, the manufacturing process is not specifically limited.

Such 3-(1-hydroxyalkyl)-camphor derivatives include:

3-(1-hydroxymethyl)-camphor,
3-(1-hydroxyethyl)-camphor,
3-(1-hydroxypropyl)-camphor,
3-(1-hydroxy-1-methyethyl)-camphor,
3-(1-hydroxybutyl)-camphor,
3-(1-hydroxy-1-methylpropyl)-camphor, and
3-(1-hydroxy-2-methylpropyl)-camphor.

These compounds are substantially odorless.

There are several stereoisomers to be applied to the present invention. However, when they are used as a noxious-insect repellent, they can be in either a singular stereoisomeric form or a mixture. From these compounds, cis and trans forms can be isolated by a column treatment or the like and separated as crystals. All of these isomers have an excellent repelling effect against noxious-insects such as mosquitoes.

These compounds to be used in the present invention are all substantially odorless.

Noxious-insect repellent compositions in various dosage forms can be prepared by blending the above-described compound as an active ingredient with a base of cosmetics or pharmaceuticals which are usually applied to human bodies or animals. They can be formulated in, for example, lotions, aerosols, milky lotions, creams or the like. These compounds can be further incorporated with other noxious-insect repellents, antioxidants, UV-absorbers, humectants or other additives.

The above compounds or the above prepared compositions of the present invention can be applied directly to human bodies or animals. Besides, substrates, such as sheets, films, nets or the like, which have preliminarily been treated with the above compound or composition by means of application, impregnation or blending, can also be used.

The quantity of the above compounds to be formulated in the noxious-insect repellents depends upon the dosage form, usage or other conditions. However, it is preferred to be generally 0.1–90%, more preferably 3–20%, by weight. The noxious-insect repellents according to the present invention are used effectively against noxious-insects, such as mosquitoes such as tiger mosquitoes, *Aedes albopictus*; black flies; ticks; millipedes; armyworms; slugs; and the like.

BEST MODE FOR CARRYING OUT THE INVENTION

The present invention will be explained hereinafter more specifically by way of synthesizing examples of the compounds applied in the present invention and working examples. In the examples, the percent is by weight unless otherwise specified.

SYNTHESIZING EXAMPLE 1

Synthesis of p-menthane-2-methyl-3,8-diol 50 g of TO was gradually added to 300 g of a 20% sulfuric acid aqueous solution and then the mixture was vigorously agitated for 20 hours. Extraction was conducted with 150 ml diethylether from this reaction solution. The diethylether layer was washed twice with 100 ml of a 10% sodium carbonate aqueous solution and then further washed twice with 100 ml of saturated brine.

This diethylether layer was dried with anhydrous sodium sulfate, and then the diethylether was removed to provide a crude reaction product. This crude reaction product was purified by means of silica gel column chromatography (eluent: hexane/ethylacetate=4/1) and 43 g of a colorless, transparent, oily substance was obtained (yield: 74.5%).

In the mass spectrometric measurement of the obtained oily substance, a peak corresponding to the loss of water from the parent ion peak was observed. In the elemental analysis, measured values of C=70.87% and H=11.93% were found (theoretical values of C and H: C=70.92% and H=11.90%). Besides, in the measurement of the infrared absorption spectrum, strong absorptions by a hydroxyl group at 3,400 cm$^{-1}$ and 1,180 cm$^{-1}$ were observed. Furthermore, absorptions by a cyclic structure at 1,480 cm$^{-1}$ and 920 cm$^{-1}$~940 cm$^{-1}$ were observed. As a result, the production of the MMD was ascertained.

SYNTHESIZING EXAMPLE 2

Synthesis of p-menthane-2-methylene-3,8-diol 50 g of DMO was gradually added to 300 g of a 20% sulfuric acid aqueous solution and then the mixture was vigorously agitated for 20 hours. Extraction was conducted with 150 ml diethylether from this reaction solution. The diethylether layer was washed twice with 100 ml of a 10% sodium carbonate aqueous solution and then further washed twice with 100 ml of saturated brine.

This diethylether layer was dried with anhydrous sodium sulfate, and then the diethylether was removed to provide a crude reaction product. This crude reaction product was purified by means of silica gel column chromatography (eluent: hexane/ethylacetate=4/1) and 43 g of a colorless, transparent, oily substance was obtained (yield: 74.5%). In the mass spectrometric measurement of the obtained oily substance, a peak corresponding to the loss of water from the parent ion peak was observed. In the elemental analysis, measured values of C=71.72% and H=10.88% were found (theoretical values of C and H: C=71.69% and H=10.94%). Besides, in the measurement of the infrared absorption spectrum, strong absorptions by a hydroxyl group at 3,400 cm$^{-1}$ and 1,180 cm$^{-1}$ were observed. Furthermore, absorptions by a cyclic structure at 1,480 cm$^{-1}$ and 920 cm$^{-1}$~940 cm$^{-1}$ were observed. As a result, the production of the MMED was ascertained.

SYNTHESIZING EXAMPLE 3

Synthesis of p-menthane-2-ethyl-3,8-diol 50 g of 2-ethyl-3,7-dimethyl-6-octenal was gradually added to 300 g of a 20% sulfuric acid aqueous solution and then the mixture was vigorously agitated for 20 hours. Extraction was conducted with 150 ml diethylether from this reaction solution. The diethylether layer was washed twice with 100 ml of a 10% sodium carbonate aqueous solution and then further washed twice with 100 ml of saturated brine. This diethylether layer was dried with anhydrous sodium sulfate, and then the diethylether was removed to provide a crude reaction product. This crude reaction product was purified by means of silica gel column chromatography (eluent: hexane/ethylacetate 4/1) and 42 g of a pale yellow, oily substance was obtained (yield: 77.3%). In the mass spectrometric measurement of the obtained oily substance, a peak corresponding to the loss of water from the parent ion peak was observed. In the elemental analysis, measured values of C=71.77% and H=12.21% were found (theoretical values of C and H: C=71.95% and H=12.08%). Thus, the production of p-menthane-2-ethyl-3,8-diol was ascertained.

SYNTHESIZING EXAMPLE 4

Synthesis of p-menthane-2-(2-propenyl)-3,8-diol 50 g of 2-(2-propenyl)-3,7-dimethyl-6-octenal was gradually added to 300 g of a 20% sulfuric acid aqueous solution and then the mixture was vigorously agitated for 20 hours. Extraction was conducted with 150 ml diethylether from this reaction solution. The diethylether layer was washed twice with 100 ml of a 10% sodium carbonate aqueous solution and then further washed twice with 100 ml of saturated brine. This diethylether layer was dried with anhydrous sodium sulfate, and then the diethylether was removed to provide a crude reaction product. This crude reaction product was purified by means of silica gel column chromatography (eluent: hexane/ethylacetate=4/1) and 41 g of a pale yellow, oily substance was obtained (yield: 76.6%). In the mass spectrometric measurement of the obtained oily substance, a peak corresponding to the loss of water from the parent ion peak was observed. In the elemental analysis, measured values of C=73.51% and H=12.04% were found (theoretical values of C and H: C=73.54% and H=11.93%). Thus, the production of p-menthane-2-(2-propenyl)-3,8-diol was ascertained.

SYNTHESIZING EXAMPLE 5

Synthesis of p-menthane-2-hexyl-3,8-diol 50 g of 2-hexyl-3,7-dimethyl-6-octenal was gradually added to 300 g of a 20% sulfuric acid aqueous solution and then the mixture was vigorously agitated for 20 hours. Extraction was conducted with 150 ml diethylether from this reaction solution. The diethylether layer was washed twice with 100 ml of a 10% sodium carbonate aqueous solution and then further washed twice with 100 ml of saturated brine. This diethylether layer was dried with anhydrous sodium sulfate, and then the diethylether was removed to provide a crude reaction product. This crude reaction product was purified by means of silica gel column chromatography (eluent: hexane/ethylacetate=4/1) and 38 g of a pale yellow, oily substance was obtained (yield: 71.1%). In the mass spectrometric measurement of the obtained oily substance, a peak corresponding to the loss of water from the parent ion peak was observed. In the elemental analysis, measured values of C=75.10% and H=12.33% were found (theoretical values of C and H: C=74.94% and H=12.58%). Thus, the production of p-menthane-2-hexyl-3,8-diol was ascertained.

SYNTHESIZING EXAMPLE 6

Synthesis of 2-hydroxymethyl-2-octyl-cyclohexanol 20 g of 2-ethoxycarbonyl-cyclohexanone was dissolved in 15 ml dimethylformamide and stirred. Then, a solution comprising 200 ml dimethylformamide with 6 g sodium hydride dispersed therein was gradually added dropwise to the above 2-ethoxycarbonyl-cyclohexanone solution. After the addition of the sodium hydride solution had been completed, the reaction solution was stirred for 2 hours at room temperature under a nitrogen gas stream. A solution comprising 15 ml dimethylformamide with 25 g octyl bromide dissolved therein was further added dropwise to the reaction solution. After the addition had been completed, the temperature was raised to 100° C. and agitation was conducted for 2 hours. The reaction solution was cooled down, then poured into iced water and extraction with 100 ml diethylether was conducted twice. The diethylether layer was dried with anhydrous sodium sulfate, and then the diethylether was removed to provide a crude reaction product of 2-ethoxycarbonyl-2-octyl-cyclohexanone. This crude reaction product was dissolved in 20 ml of tetrahydrofuran. A solution comprising 80 ml tetrahydrofuran with 2 g lithium borohydride dispersed therein was added dropwise to the above 2-ethoxycarbonyl-2-octyl-cyclohexanone solution under an iced condition while stirring and the stirring was continued for 4 hours. After adding 50 ml ethylacetate and 100 ml distilled water, the solution was acidified by the addition of a 10% sulfuric acid aqueous solution to give a pH of 2. The reaction solution was extracted twice with 50 ml of diethylether. The diethylether layer was dried with anhydrous sodium sulfate, and then the diethylether was removed to provide a crude reaction product of 2-hydroxymethyl-2-octyl-cyclohexanone. This crude reaction product was purified by means of silica gel column chromatography (eluent: chloroform/methanol=97/3) and 18.3 g of 2-hydroxymethyl-2-octyl-cyclohexanol was obtained as a pale yellow, oily substance (yield: 64.3%). In the measurement of the infrared absorption spectrum, a strong absorption by a hydroxyl group at 3,370 $cm^{-1}$ and, in the mass spectrometric measurement, a peak corresponding to the loss of water from the parent ion peak, were observed. Besides, in the elemental analysis, measured values of C=74.27% and H=12.53% were found (theoretical values of C and H: C=74.33% and H=12.74%). Thus, the production of 2-hydroxymethyl-2-octyl-cyclohexanol was ascertained.

SYNTHESIZING EXAMPLE 7

Synthesis of 2-hydroxymethyl-2-ethyl-cyclohexanol

The same procedure as Synthesizing Example 6 was conducted, except that 12 g of ethyl bromide was used instead of 25 g of octyl bromide used in Synthesizing Example 6, and 14.7 g of 2-hydroxymethyl-2-ethyl-cyclohexanol was obtained as a pale yellow, oily substance (yield: 79%). The identification of the structure was conducted in the same manner as Synthesizing Example 6, with the consequence that the structure was affirmed. It was further identified by an elemental analysis in which measured values of C=68.13% and H=11.53% were found (theoretical values of C and H: C=68.31% and H=11.47%).

SYNTHESIZING EXAMPLE 8

Synthesis of 2-hydroxymethyl-2-isopropyl-cyclohexanol

The same procedure as Synthesizing Example 6 was conducted, except that 15 g of isopropyl bromide was used instead of 25 g of octyl bromide used in Synthesizing Example 6, and 14.8 g of 2-hydroxymethyl-2-isopropyl-cyclohexanol was obtained as a pale yellow, oily substance (yield: 73%). The identification of the structure was conducted in the same manner as Synthesizing Example 6, with the consequence that the structure was supported. It was further identified by an elemental analysis in which measured values of C=69.77% and H=11.59% were found (theoretical values of C and H: C=69.72% and H=11.70%).

SYNTHESIZING EXAMPLE 9

Synthesis of 2-hydroxymethyl-2-undecyl-cyclohexanol

The same procedure as Synthesizing Example 6 was conducted, except that 15 g of undecyl bromide was used instead of the 25 g of octyl bromide used in Synthesizing Example 6, and 21.2 g of 2-hydroxymethyl-2-undecyl-cyclohexanol was obtained as a pale yellow, oily substance (yield: 60%). The identification of the structure was conducted in the same manner as Synthesizing Example 6, with the consequence that the structure was affirmed. It was further identified by an elemental analysis in which measured values of C=79.67% and H=12.56% were found (theoretical values of C and H: C=79.45% and H=12.83%).

SYNTHESIZING EXAMPLE 10

Synthesis of 2-hydroxymethyl-2-octyl-cyclopentanol 20 g of 2-ethoxycarbonyl-cyclopentanone was dissolved in 15 ml dimethylformamide and stirred. Then, a solution comprising 200 ml dimethylformamide with 6 g sodium hydride dispersed therein was gradually added dropwise to the above 2-ethoxycarbonyl-cyclopentanone solution. After the addition of the sodium hydride solution had been completed, the reaction solution was stirred for 2 hours at room temperature under a nitrogen gas stream. A solution comprising 15 ml dimethylformamide with 25 g octyl bromide dissolved therein was further added dropwise to the reaction solution. After the addition had been completed, the temperature was raised to 100° C. and agitation was conducted for 2 hours. The reaction solution was cooled down, then poured into iced water and extraction with 100 ml diethylether was conducted twice. The diethylether layer was dried with anhydrous sodium sulfate, and then the diethylether was removed to provide a crude reaction product of 2-ethoxycarbonyl-2-octyl-cyclopentanone. This crude reaction product was dissolved in 20 ml of tetrahydrofuran. A solution comprising 80 ml tetrahydrofuran with 2 g lithium borohydride dispersed therein was added dropwise to the above 2-ethoxycarbonyl-2-octyl-cyclopentanone solution under an iced condition while stirring and the stirring was further continued for 4 hours. After adding 50 ml ethylacetate and 100 ml distilled water, the solution was acidified by the addition of a 10% sulfuric acid aqueous solution to give a pH of 2. The reaction solution was extracted twice with 50 ml of diethylether. The diethylether layer was dried with anhydrous sodium sulfate, and then the diethylether was removed to provide a crude reaction product of 2-hydroxymethyl-2-octyl-cyclopentanone. This crude reaction product was purified by means of silica gel column chromatography (eluent: chloroform/methanol=97/3) and 18.9 g of 2-hydroxymethyl-2-octyl-cyclopentanol was obtained as a pale yellow, oily substance (yield: 64.7%). In the measurement of the infrared absorption spectrum, a strong absorption by a hydroxyl group at 3,370 cm$^{-1}$ and, in the mass spectrometric measurement, a peak corresponding to the loss of water from the parent ion peak, were observed. Besides, in the elemental analysis, measured values of C=73.37% and H=12.45% were found (theoretical values of C and H: C=73.13% and H=12.35%). Thus, the production of 2-hydroxymethyl-2-octyl-cyclopentanol was ascertained.

SYNTHESIZING EXAMPLE 11

Synthesis of 2-hydroxymethyl-2-ethyl-cyclopentanol

The same procedure as Synthesizing Example 10 was conducted, except that 12 g of ethyl bromide was used instead of 25 g of octyl bromide used in Synthesizing Example 10, and 12.4 g of 2-hydroxymethyl-2-ethyl-cyclopentanol was obtained as a pale yellow, oily substance (yield: 67%). The identification of the structure was conducted in the same manner as Synthesizing Example 10, with the consequence that the structure was affirmed. It was further identified by an elemental analysis in which measured values of C=66.50% and H=11.32% were found (theoretical values of C and H: C=66.63% and H=11.18%).

SYNTHESIZING EXAMPLE 12

Synthesis of 2-hydroxymethyl-2-isopropyl-cyclopentanol

The same procedure as Synthesizing Example 10 was conducted, except that 15 g of isopropyl bromide was used instead of 25 g of octyl bromide used in Synthesizing Example 10, and 12.8 g of 2-hydroxymethyl-2-isopropyl-cyclopentanol was obtained as a pale yellow, oily substance (yield: 63%). The identification of the structure was conducted in the same manner as Synthesizing Example 10, with the consequence that the structure was affirmed. It was further identified by an elemental analysis in which measured values of C=68.11% and H=11.60% were found (theoretical values of C and H: C=68.31% and H=11.46%).

SYNTHESIZING EXAMPLE 13

Synthesis of 2-hydroxymethyl-2-undecyl-cyclopentanol

The same procedure as Synthesizing Example 10 was conducted, except that 15 g of undecyl bromide was used instead of 25 g of octyl bromide used in Synthesizing Example 10, and 24.0 g of 2-hydroxymethyl-2-undecyl-cyclopentanol was obtained as a pale yellow, oily substance (yield: 66%). The identification of the structure was conducted in the same manner as Synthesizing Example 10, with the consequence that the structure was affirmed. It was further identified by an elemental analysis in which measured values of C=76.02% and H=12.81% were found (theoretical values of C and H: C=76.00% and H=12.76%).

SYNTHESIZING EXAMPLE 14

Synthesis of 2-hydroxymethyl-menthol 8 g of sodium hydride (containing 40% of liquid paraffin) was gradually added to 100 ml of dry benzene and 20 g of diethyl carbonate was further added therein. Then the mixture was heated to the reflux temperature, while stirring. A solution comprising 40 ml dry benzene and 15 g menthone dissolved therein was gradually added dropwise to this reaction solution, taking about 2 hours. After the whole amount had been added, the heating while stirring was further continued for 2 hours.

The mixture was cooled down to room temperature and then 20 ml of acetic acid was gradually added thereto. 100 ml of cold water was further added and then the organic layer was extracted. The water layer was extracted twice with 100 ml of benzene and then the above organic layer was admixed. This organic layer was washed with cold water and then dried with anhydrous sodium sulfate. Then, the benzene was removed to provide a crude reaction product. This crude reaction product was vacuum-distilled, whereby 16 g of a fraction mainly containing 2-ethoxycarbonyl-menthone was obtained.

This fraction was dissolved in 20 ml of dry tetrahydrofuran (THF) and then the resulting solution, while stirring under a cold condition, was gradually admixed dropwise to a solution comprising 120 ml dry THF with 2 g lithium borohydride dispersed therein. After the admixing had been completed, the stirring was continued for 4 hours at room temperature. Under cooling and stirring, 50 ml of ethyl acetate and 100 ml of water were gradually added and then the solution was acidified by the addition of a 10% sulfuric acid aqueous solution to give a pH of 2.

The reaction solution was extracted twice with 100 ml of diethylether and then dried with anhydrous sodium sulfate. Then, the diethylether and THF were removed to provide a crude reaction product. By purifying by means of silica gel column chromatography (eluent: benzene/acetone=8/1), 8.3 g of a colorless, oily substance was obtained (yield: 34.4%).

In the mass spectrometric measurement of the obtained oily substance, a peak corresponding to the loss of water from the parent ion peak was observed. In the measurement of the infrared absorption spectrum, a strong absorption by a hydroxyl group at 3,380 cm$^{-1}$ was found. Besides, the production of HMMO was ascertained by the elemental analysis in which measured values of C=70.85% and H=12.01% were found (theoretical values of C and H: C=70.92% and H=11.90%).

SYNTHESIZING EXAMPLE 15

Synthesis of 2-hydroxymethyl-4-(t-butyl)-cyclohexanol 20 g of 2-ethoxycarbonyl-4-(t-butyl)-cyclohexanone was dissolved in 20 ml tetrahydrofuran. A solution comprising 80 ml tetrahydrofuran with 2 g lithium borohydride dispersed therein was gradually added dropwise to the above 2-ethoxycarbonyl-4-(t-butyl)-cyclohexanone solution while stirring under an iced condition. The stirring was continued for 4 hours. After adding 50 ml ethylacetate and 100 ml distilled water, the solution was acidified by the addition of a 10% sulfuric acid aqueous solution to give a pH of 2. The reaction solution was extracted twice with 50 ml of diethylether.

The diethylether layer was dried with anhydrous sodium sulfate, and then the diethylether was removed to provide a crude reaction product of 2-hydroxymethyl-4-(t-butyl)-cyclohexanol. This crude reaction product was purified by means of silica gel column chromatography (eluent: chloroform/methanol=97/3) and 15.3 g of 2-hydroxymethyl-4-(t-butyl)-cyclohexanol was obtained as a colorless, oily substance (yield: 93%). In the measurement of the infrared absorption spectrum, a strong absorption by a hydroxyl group at 3,370 cm$^{-1}$ and, in the mass spectrometric measurement, a peak corresponding to the loss of water from the parent ion peak, were observed. Besides, in the mass spectrometric measurement of the trimethyl silyl derivative (TMS) of the obtained substance, a parent ion peak of 310 was found. In the elemental analysis, measured values of C=70.78% and H=11.93% were found (theoretical values of C and H: C=70.92% and H=11.90%). Thus, the production of 2-hydroxymethyl-4-(t-butyl)-cyclohexanol was ascertained.

SYNTHESIZING EXAMPLE 16

Synthesis of 2-hydroxymethyl-cyclooctanol

The same procedure as Synthesizing Example 15 was conducted, except that 20 g of 2-ethoxycarbonyl-cyclooctanone was used instead of 20 g of 2-ethoxycarbonyl-4-(t-butyl)-cyclohexanone used in Synthesizing Example 15, and 14.5 g of 2-hydroxymethyl-2-cyclooctanol was obtained as a colorless, oily substance (yield: 91%). The identification of the structure was conducted by the mass spectrometric measurement in the same manner as Synthesizing Example 15, with the consequence that the structure was affirmed. It was further identified by an elemental analysis in which measured values of C=67.96% and H=11.58% were found (theoretical values of C and H: C=68.31% and H=11.47%).

SYNTHESIZING EXAMPLE 17

Synthesis of 2-hydroxymethyl-4-ethyl-cyclopentanol

The same procedure as Synthesizing Example 15 was conducted except that 20 g of 2-ethoxycarbonyl-4-ethyl-cyclopentanone was used instead of 20 g of 2-ethoxycarbonyl-4-(t-butyl)-cyclohexanone used in Synthesizing Example 15, and 13.6 g of 2-hydroxymethyl-4-ethyl-cyclopentanol was obtained as a colorless, oily substance (yield: 87%). The identification of the structure was conducted by the mass spectrometric measurement in the same manner as Synthesizing Example 15, with the consequence that the structure was affirmed. It was further identified by an elemental analysis in which measured values of C=66.33% and H=11.41% were found (theoretical values of C and H: C=66.63% and H=11.18%).

SYNTHESIZING EXAMPLE 18

Synthesis of 2-hydroxymethyl-3,4-dimethyl-cyclohexanol

The same procedure as Synthesizing Example 15 was conducted, except that 15 g of 2-ethoxycarbonyl-3,4-dimethyl-cyclohexanone was used instead of 20 g of 2-ethoxycarbonyl-4-(t-butyl)-cyclohexanone used in Synthesizing Example 15, and 9.3 g of 2-hydroxymethyl-3,4-dimethyl-cyclohexanol was obtained as a colorless, oily substance (yield: 78%). The identification of the structure was conducted by the mass spectrometric measurement in the same manner as Synthesizing Example 15, with the consequence that the structure was affirmed. It was further identified by an elemental analysis in which the values of C=68.10 and H=11.64% were found (theoretical values of C and H: C=68.31% and H=11.47%).

SYNTHESIZING EXAMPLE 19

Synthesis of 2-hydroxymethyl-4-isopropyl-6-methyl-cyclohexanol

The same procedure as Synthesizing Example 15 was conducted, except that 20 g of 2-ethoxycarbonyl-4-isopropyl-6-methyl-cyclohexanone was used instead of 20 g of 2-ethoxycarbonyl-4-(t-butyl)-cyclohexanone used in Synthesizing Example 15, and 13.5 g of 2-hydroxymethyl-4-isopropyl-6-methyl-cyclohexanol was obtained as a colorless, oily substance (yield: 82%). The identification of the structure was conducted by the mass spectrometric measurement in the same manner as Synthesizing Example 15, with the consequence that the structure was affirmed. It was further identified by an elemental analysis in which measured values of C=70.86% and H=12.05% were found (theoretical values of C and H: C=70.92% and H=11.90%).

SYNTHESIZING EXAMPLE 20

Synthesis of 3-(1-hydroxyethyl)-borneol 2.50 ml of 2.5M n-butylithium hexane solution was added dropwise to a tetrahydrofuran solution comprising 4 ml THF and 1.00 ml diisopropylamine at −78° C. and the mixture was stirred for 15 minutes. Then, a solution comprising 4 ml THF with 0.91 g camphor dissolved therein was added dropwise to the above solution at −78° C., then, 0.27 g of acetaldehyde was further added and the mixture was stirred for 15 minutes. Thus, 3-(1-hydroxyethyl)-camphor was synthesized. This reaction solution was admixed with 50 ml of saturated sodium hydrogen carbonate aqueous solution and restored to room temperature. The reaction product was extracted with diethylether. 5 ml of the above 3-(1-hydroxyethyl)-camphor diethylether solution was gradually added dropwise to 10 ml of a diethylether solution comprising 10 ml diethylether and 0.11 g lithium aluminum hydride and the mixture was stirred at room temperature for 30 minutes. 0.5 ml of water and 0.5 ml of 2N-NaOH were added to the reaction solution to separate the solids out. The separated-out solids were filtered off and the solvent was removed under vacuum. The residue was purified by means of silica gel column chromatography (eluent: hexane/ethylacetate=7/3) and 0.75 g of 3-(1-hydroxyethyl)-borneol was obtained (yield: 95%).

SYNTHESIZING EXAMPLE 21

Synthesis of 3-(1-hydroxypropyl)-borneol

Synthesis was conducted in the same procedure as Synthesizing Example 20, except that 0.35 g of propionaldehyde was used instead of acetaldehyde and 0.79 g of 3-(1-hydroxypropyl)-camphor was obtained (yield: 63%). Successively thereafter, using 0.84 g of the 3-(1-hydroxypropyl)-camphor, synthesis was conducted also in the same procedure as Synthesizing Example 20 and 0.80 g of 3-(1-hydroxypropyl)-borneol was obtained (yield: 94%).

SYNTHESIZING EXAMPLE 22

Synthesis of 3-(1-hydroxy-2-methylpropyl)-borneol

Synthesis was conducted in the same procedure as Synthesizing Example 20, except that 0.44 g of 2-methyl-propionaldehyde was used instead of acetaldehyde and 0.86 g of 3-(1-hydroxy-2-methylpropyl),-camphor was obtained (yield: 64%). Successively thereafter, using 0.90 g of the 3-(1-hydroxy-2-methylpropyl)-camphor, synthesis was conducted also in the same procedure as Synthesizing Example 20 and 0.85 g of 3-(1-hydroxy-2-methylpropyl)-borneol was obtained (yield: 94%).

SYNTHESIZING EXAMPLE 23

Synthesis of 3-(1-hydroxybutyl)-borneol

Synthesis was conducted in the same procedure as Synthesizing Example 20, except that 0.44 g of butylaldehyde was used instead of acetaldehyde and 0.79 g of 3-(1-hydroxybutyl)-camphor was obtained (yield: 59%). Successively thereafter, using 0.90 g of the 3-(1-hydroxybutyl)-camphor, synthesis was conducted also in the same procedure as Synthesizing Example 20 and 0.81 g of 3-(1-hydroxybutyl)-borneol was obtained (yield: 90%).

SYNTHESIZING EXAMPLE 24

Synthesis of 2-hydroxymethyl-menthone 20 g of menthone was dissolved in 50 ml of methanol and then 1.6 g of potassium carbonate was admixed therewith. The reaction solution was heated up to 65° C. and 14 ml of formalin solution was gradually added dropwise thereto, while stirring. After the whole quantity of the formalin solution had been added, the stirring was continued for 3 hours. Methanol was removed from this reaction solution under a vacuum and then extraction was conducted twice with 50 ml of diethylether. The diethylether layer was dried with anhydrous sodium sulfate and then diethylether was removed to provide a crude reaction product. This crude reaction product was purified by means of silica gel column chromatography (eluent: benzene/acetone=8/1) and 7.3 g of a colorless and transparent, oily substance was obtained (yield: 30.5%).

In the mass spectrometric measurement of the resulting oily substance, a peak corresponding to the loss of water from the parent ion peak was observed. Besides, in the mass spectrometric measurement of the trimethyl silyl derivative of the obtained substance, a parent ion peak of 256 was observed. In the elemental analysis, measured values of C=71.43% and H=11.08% were found (theoretical values of C and H: C=71.69% and H=10.94%). Thus, the production of HMMT was ascertained.

SYNTHESIZING EXAMPLE 25

Synthesis of 2-(1-hydroxyisopropyl)-5-methyl-cyclopentanone 7.9 g of 2-(1-hydroxyisopropyl)-5-methyl-cyclopentanol was added dropwise to 100 ml of a dichloromethane suspension containing 16.2 g pyridinium chlorochromate and the mixture was stirred for 5 hours at room temperature. The reaction solution was admixed with diethylether and stirred. Then, the chromate was filtered out and the filtrate was condensed under a vacuum. The residue was purified by means of silica gel column chromatography (eluent: hexane/ethylacetate=7/3) and 6.6 g of 2-(1-hydroxyisopropyl)-5-methyl-cyclopentanone was obtained as an oily substance (yield: 86%).

In the mass spectrometric measurement of the obtained oily substance, a molecular ion peak (M$^+$) was observed. Furthermore, two peaks corresponding to the loss of water and methyl group from the parent ion peak were observed. In the elemental analysis, measured values of C=69.15% and H=10.19% were found (theoretical values of C and H: C=69.20% and H=10.32%). Besides, in the measurement of the infrared absorption spectrum, a strong absorption by carbonyl group at 1,720 cm$^{-1}$ was observed. From the results of the above analyses, the production of 2-(1-hydroxyisopropyl)-5-methyl-cyclopentanone was ascertained.

SYNTHESIZING EXAMPLE 26

Synthesis of 8-hydroxy-2-methyl-p-menthan-3-one 9.3 g of p-menthane-2-methyl-3,8-diol obtained in the above Synthesizing Example 1 was added dropwise to 100 ml of a dichloromethane suspension containing 16.2 g pyridinium chlorochromate, and the mixture was stirred for 5 hours at room temperature. The reaction solution was admixed with diethylether and stirred. Then, the chromate was filtered out and the filtrate was condensed under a vacuum. The residue was purified by means of silica gel column chromatography (eluent: hexane/ethylacetate=4/1) and 7.9 g of 8-hydroxy-2-methyl-p-menthan-3-one of the present invention was obtained as an oily substance (yield: 85.9%).

In the mass spectrometric measurement of the obtained oily substance, a molecular ion peak (M$^+$) and a peak corresponding to the loss of water from the parent ion peak were observed. In the elemental analysis, measured values of C=71.68% and H=10.93% were found (theoretical values of C and H: C=71.70% and H=10.93%). Besides, in the measurement of the infrared absorption spectrum, an absorption by a hydroxyl group at 3,400 cm$^{-1}$ and a strong absorption by a carbonyl group at 1,720 cm$^{-1}$ were observed. From the results of the above analyses, the production of 8-hydroxy-2-methyl-p-menthan-3-one was ascertained. This product was substantially odorless.

SYNTHESIZING EXAMPLE 27

Synthesis of 8-hydroxy-2-methylene-p-menthan-3-one 9.2 g of p-menthane-2-methylene-3,8-diol obtained in the above Synthesizing Example 2 was added dropwise to 100 ml of a dichloromethane suspension containing 16.2 g pyridinium chlorochromate, and the mixture was stirred for 5 hours at room temperature. The reaction solution was admixed with diethylether and stirred. Then, the chromate was filtered out and the filtrate was condensed under a vacuum. The residue was purified by means of silica gel column chromatography (eluent: hexane/ethylacetate=4/1) and 7.0 g of 8-hydroxy-2-methylene-p-menthan-3-one of the present invention was obtained as an oily substance (yield: 76.9%).

In the mass spectrometric measurement of the obtained oily substance, a molecular ion peak (M$^+$) and a peak corresponding to the loss of water from the parent ion peak were observed. In the elemental analysis, measured values of C=72.52% and H=9.90% were found (theoretical values of C and H: C=72.49% and H=9.95%). Besides, in the measurement of the infrared absorption spectrum, an absorption by a hydroxyl group at 3,400 cm$^{-1}$ and a strong absorption by a carbonyl group at 1,720 cm$^{-1}$ were observed. From the results of the above analyses, the production of 8-hydroxy-2-methylene-p-menthan-3-one was ascertained. This product was substantially odorless.

SYNTHESIZING EXAMPLE 28

Synthesis of 8-hydroxy-2-ethyl-p-menthan-3-one 10.0 g of p-menthane-2-ethyl-3,8-diol obtained in the above Synthesizing Example 3 was added dropwise to 100 ml of a dichloromethane suspension containing 16.2 g pyridinium chlorochromate, and the mixture was stirred for 5 hours at room temperature. The reaction solution was admixed with diethylether and stirred. Then, the chromate was filtered out and the filtrate was condensed under vacuum. The residue was purified by means of silica gel column chromatography (eluent: hexane/ethylacetate=4/1) and 8.2 g of 8-hydroxy-2-ethyl-p-menthan-3-one of the present invention was obtained as an oily substance (yield: 82.8%).

In the mass spectrometric measurement of the obtained oily substance, a molecular ion peak ($M^+$) and a peak corresponding to the loss of water from the parent ion peak were observed. In the elemental analysis, measured values of C=72.75% and H=11.22% were found (theoretical values of C and H: C=72.69% and H=11.18%). Besides, in the measurement of the infrared absorption spectrum, an absorption by a hydroxyl group at 3,400 $cm^{-1}$ and a strong absorption by a carbonyl group at 1,720 $cm^{-1}$ were observed. From the results of the above analyses, the production of 8-hydroxy-2-ethyl-p-menthan-3-one was ascertained. This product was substantially odorless.

SYNTHESIZING EXAMPLE 29

Synthesis of 8-hydroxy-2-(2-propenyl)-p-menthan-3-one 10.6 g of p-menthan-2-(2-propenyl)-3,8-diol obtained in the above Synthesizing Example 4 was added dropwise to 100 ml of a dichloromethane suspension containing 16.2 g pyridinium chlorochromate, and the mixture was stirred for 5 hours at room temperature. The reaction solution was admixed with diethylether and stirred. Then, the chromate was filtered out and the filtrate was condensed under a vacuum. The residue was purified by means of silica gel column chromatography (eluent: hexane/ethylacetate=4/1) and 8.6 g of 8-hydroxy-2-(2-propenyl)-p-menthan-3-one of the present invention was obtained as an oily substance (yield: 81.9%).

In the mass spectrometric measurement of the obtained oily substance, a molecular ion peak ($M^+$) and a peak corresponding to the loss of water from the parent ion peak were observed. In the elemental analysis, measured values of C=74.20% and H=10.60% were found (theoretical values of C and H: C=74.25% and H=10.54%). Besides, in the measurement of the infrared absorption spectrum, an absorption by a hydroxyl group at 3,400 $cm^{-1}$ and a strong absorption by a carbonyl group at 1,720 $cm^{-1}$ were observed. From the results of the above analyses, the production of 8-hydroxy-2-(2-propenyl)-p-menthan-3-one was ascertained. This product was substantially odorless.

SYNTHESIZING EXAMPLE 30

Synthesis of 8-hydroxy-2-hexyl-p-menthan-3-one 12.8 g of p-menthane-2-hexyl-3,8-diol obtained in the above Synthesizing Example 5 was added dropwise to 100 ml of a dichloromethane suspension containing 16.2 g pyridinium chlorochromate, and the mixture was stirred for 5 hours at room temperature. The reaction solution was admixed with diethylether and stirred. Then, the chromate was filtered out and the filtrate was condensed under a vacuum. The residue was purified by means of silica gel column chromatography (eluent: hexane/ethylacetate=4/1) and 10.8 g of 8-hydroxy-2-hexyl-p-menthan-3-one of the present invention was obtained as an oily substance (yield: 85.0%).

In the mass spectrometric measurement of the obtained oily substance, a molecular ion peak ($M^+$) and a peak corresponding to the loss of water from the parent ion peak were observed. In the elemental analysis, measured values of C=75.50% and H=11.94% were found (theoretical values of C and H: C=75.54% and H=11.88%). Besides, in the measurement of the infrared absorption spectrum, an absorption by a hydroxyl group at 3,400 $cm^{-1}$ and a strong absorption by a carbonyl group at 1,720 $cm^{-1}$ were observed. From the results of the above analyses, the production of 8-hydroxy-2-hexyl-p-menthan-3-one was ascertained. This product was substantially odorless.

SYNTHESIZING EXAMPLE 31

Synthesis of 3-(1-hydroxyethyl)-camphor 2.50 ml of 2.5 M n-butylithium hexane solution was added dropwise a tetrahydrofuran solution comprising 4 ml THF and 1.00 ml diisopropylamine at −78° C. and the mixture was stirred for 15 minutes. Then, a THF solution comprising 4 ml THF and 0.91 g camphor was added dropwise to the above solution at −78° C., then the solution was further admixed with 0.27 g of acetaldehyde and stirred for 15 minutes. This reaction solution was admixed with 50 ml of a saturated sodium hydrogen carbonate aqueous solution and restored to room temperature. The reaction product was extracted with diethylether. The organic layer was washed with saturated brine, dried with anhydrous sodium sulfate and then the solvent was removed under a vacuum. The residue was purified by means of silica gel column chromatography (eluent: hexane/ethylacetate=8/2) and 0.94 g of 3-(1-hydroxyethyl)-camphor was obtained (yield: 80%).

SYNTHESIZING EXAMPLE 32

Synthesis of 3-(1-hydroxypropyl)-camphor

Synthesis was conducted in the same procedure as Synthesizing Example 31, except that 0.35 g of propionaldehyde was used instead of acetaldehyde, and 0.79 g of 3-(1-hydroxypropyl)-camphor was obtained (yield: 63%).

SYNTHESIZING EXAMPLE 33

Synthesis of 3-(1-hydroxy-2-methylpropyl)-camphor

Synthesis was conducted in the same procedure as Synthesizing Example 31, except that 0.44 g of 2-methylpropionaldehyde was used instead of acetaldehyde, and 0.86 g of 3-(1-hydroxy-2-methylpropyl)-camphor was obtained (yield: 64%).

SYNTHESIZING EXAMPLE 34

Synthesis of 3-(1-hydroxybutyl)-camphor

Synthesis was conducted in the same procedure as Synthesizing Example 31, except that 0.44 g of butyl aldehyde was used instead of acetaldehyde, and 0.79 g of 3-(1-hydroxybutyl)-camphor was obtained (yield: 59%).

The present invention will be illustrated by the following examples.

In each example, the noxious-insect repellency test was conducted as follows:

Test method of noxious-insect repelling effect and durability thereof In order to assess the repelling effect against imagoes of the tiger mosquito, Aedes albopictus, the following test was conducted at a room temperature of 30° C. and a relative humidity of 70% in an air-conditioned room. 10 ml each of test samples was applied to left and right forearms. Each treated forearm was introduced into a wire gauze cage (20 cm L.×15 cm Dia.) containing 50 female and 50 male tiger mosquitoes 5–7 days old after eclosion, for 15 minutes to afford time for biting. The assessment was repeated 30 minutes, 1 hour, 2 hours, 4 hours and 6 hours after the test sample was applied. The number of marks made by biting within each biting time was counted and a percent repellency was calculated using the following formula:

Percent repellency=(X−Y)/X×100 (%)

X: the number of the marks made by biting when the test sample was not applied,

Y: the number of the marks made by biting when the test sample was applied.

Examples 1 and 2, and Comparative Examples 1 and 2 (Repellent lotion)

The p-menthane-2-methyl-3,8-diol (MMD) and p-menthane-2-methylene-3,8-diol (MMED) obtained in the foregoing Synthesizing Examples 1 and 2, respectively, were formulated according to the recipe shown in Table 1 below to prepare repellent lotions of Examples 1 and 2. The noxious-insect repellency test was conducted with these repellent lotions. The N,N-diethyltoluamide formulated in Comparative Example 1 is a hitherto known compound used as a noxious-insect repellent, and the p-menthane-3,8-diol formulated in Comparative Example 2 is a compound known to have an excellent repelling effect (the same in the Comparative Examples hereinafter).

TABLE 1

| Synthetic component | Example | | Comparative Example | |
|---|---|---|---|---|
| | 1 | 2 | 1 | 2 |
| 95° non-denatured alcohol | 89 | 87 | 87 | 85 |
| Pure water | 10 | 10 | 10 | 10 |
| N,N-diethyltoluamide | — | — | 3 | — |
| p-Menthane-3,8-diol | — | — | — | 3 |
| MMD (compound of Synthesizing Example 1) | 3 | — | — | — |
| MMED (compound of Synthesizing Example 2) | — | 3 | — | — |

Unit: wt. %

With respect to the repellents of the above Examples 1 and 2 and Comparative Examples 1 and 2, the noxious-insect repellency test was conducted against the above tiger mosquito imagoes. The results are shown in Table 2. As evident from Table 2, the repellent lotions of the present invention, formulated with the MMD and MMED, respectively, exhibited an excellent noxious-insect repelling effect and durability.

TABLE 2

| After application | 30 min. | 1 hr. | 4 hrs. | 6 hrs. |
|---|---|---|---|---|
| Example 1 | 100 | 100 | 100 | 95 |
| Example 2 | 100 | 100 | 100 | 100 |
| Comparative Example 1 | 100 | 78 | 68 | 40 |
| Comparative Example 2 | 100 | 85 | 75 | 35 |

Unit: %

EXAMPLES 3, 4 AND 5, AND COMPARATIVE EXAMPLES 3 AND 4 (Repellent lotion)

The p-menthane-2-ethyl-3,8-diol, p-menthane-2-(2-propenyl)-3,8-diol and p-menthane-2-hexyl-3,8-diol20 obtained in the foregoing Synthesizing Examples 3, 4 and 5, respectively, were formulated according to the recipe shown in Table 3 below to prepare repellent lotions of Examples 3, 4 and 5.

TABLE 3

| Synthetic component | Comparative Example | | Example | | |
|---|---|---|---|---|---|
| | 3 | 4 | 3 | 4 | 5 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| p-Menthane-3,8-diol | — | 3 | — | — | — |
| p-Menthane-2-ethyl-3,8-diol | — | — | 3 | — | — |
| p-Menthane-2-(2-propenyl)-3,8-diol | — | — | — | 3 | — |
| p-Menthane-2-hexyl-3,8-diol | — | — | — | — | 3 |

Unit: wt. %

The noxious-insect repellency test against tiger mosquito imagoes was conducted with these repellent lotions, and Examples 3, 4 and 5 were compared with Comparative Examples 3 and 4. The results are shown in Table 4. As evident from Table 4, the repellent lotions of the present invention formulated with p-menthane-2-ethyl-3,8-diol, p-menthane-2-(2-propenyl)-3,8-diol and p-menthane-2-hexyl-3,8-diol, respectively, exhibited an excellent noxious-insect repelling effect and durability.

TABLE 4

| After application | 30 min. | 1 hr. | 4 hrs. | 6 hrs. |
|---|---|---|---|---|
| Comparative Example 3 | 100 | 78 | 68 | 40 |
| Comparative Example 4 | 100 | 100 | 75 | 55 |
| Example 3 | 100 | 100 | 100 | 100 |
| Example 4 | 100 | 100 | 100 | 100 |
| Example 5 | 100 | 95 | 87 | 95 |

Unit: %

EXAMPLES 6–9, AND COMPARATIVE EXAMPLES 5 (Repellent lotion)

The 2-hydroxymethyl-2-ethyl-cyclohexanol, 2-hydroxymethyl-2-octyl-cyclohexanol, 2-hydroxymethyl-2-isopropyl-cyclohexanol and 2-hydroxymethyl-2-undecyl-cyclohexanol obtained in the foregoing Synthesizing Examples 6–9, respectively, were formulated according to the recipe shown in Table 5 below to prepare repellent lotions of Examples 6–9, and the noxious-insect repellency test was conducted.

TABLE 5

| Synthetic component | Comparative Example | Example | | | |
|---|---|---|---|---|---|
| | 5 | 6 | 7 | 8 | 9 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-Hydroxymethyl-2-ethyl-cyclohexanol | — | 3 | — | — | — |
| 2-Hydroxymethyl-2-octyl-cyclohexanol | — | — | 3 | — | — |

TABLE 5-continued

|  | Comparative Example | Example | | | |
|---|---|---|---|---|---|
| Synthetic component | 5 | 6 | 7 | 8 | 9 |
| 2-Hydroxymethyl-2-isopropyl-cyclohexanol | — | — | — | 3 | — |
| 2-Hydroxymethyl-2-undecyl-cyclohexnol | — | — | — | — | 3 |

Unit: wt. %

The noxious-insect repellency test against tiger mosquito imagoes was conducted with these repellent lotions, and Examples 6–9 were compared with Comparative Example 5. The results are shown in Table 6. As evident from Table 6, the repellent lotions of the present invention formulated with 2-hydroxymethyl-2-ethyl-cyclohexanol, 2-hydroxymethyl-2-octyl-cyclohexanol, 2-hydroxymethyl-2-isopropyl-cyclohexanol and 2-hydroxymethyl-2-undecyl-cyclohexanol, respectively, exhibited an excellent noxious-insect repelling effect and durability.

TABLE 6

| After application | 30 min. | 1 hr. | 4 hrs. | 6 hrs. |
|---|---|---|---|---|
| Comparative Example 5 | 100 | 78 | 68 | 40 |
| Example 6 | 100 | 100 | 100 | 88 |
| Example 7 | 100 | 100 | 100 | 100 |
| Example 8 | 100 | 100 | 100 | 100 |
| Example 9 | 100 | 96 | 94 | 96 |

Unit: %

EXAMPLES 10–13, AND COMPARATIVE EXAMPLES 6 (Repellent lotion)

The 2-hydroxymethyl-2-ethyl-cyclopentanol, 2-hydroxyethyl-2-octyl-cyclopentanol, 2-hydroxymethyl-2-isopropyl-cyclopentanol and 2-hydroxymethyl-2-undecyl-cyclopentanol obtained in the foregoing Synthesizing Examples 10–13, respectively, were formulated according to the recipe shown in Table 7 below to prepare repellent lotions of Examples 10–13, and the noxious-insect repellency test was conducted.

TABLE 7

|  | Comparative Example | Example | | | |
|---|---|---|---|---|---|
| Synthetic component | 6 | 10 | 11 | 12 | 13 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-Hydroxymethyl-2-ethyl-cyclopentanol | — | 3 | — | — | — |
| 2-Hydroxymethyl-2-octyl-cyclopentanol | — | — | 3 | — | — |
| 2-Hydroxymethyl-2-isopropyl-cyclopentanol | — | — | — | 3 | — |
| 2-Hydroxymethyl-2-undecyl-cyclopentanol | — | — | — | — | 3 |

Unit: wt. %

The noxious-insect repellency test against tiger mosquito imagoes was conducted with these repellent lotions, and Examples 10–13 were compared with Comparative Example 6. The results are shown in Table 8. As evident from Table 8, the repellent lotions of the present invention formulated with 2-hydroxymethyl-2-ethyl-cyclopentanol, 2-hydroxymethyl-2-octyl-cyclopentanol, 2-hydroxymethyl-2-isopropyl-cyclopentanol and 2-hydroxymethyl-2-undecyl-cyclopentanol, respectively, exhibited an excellent noxious-insect repelling effect and durability.

TABLE 8

| After application | 30 min. | 1 hr. | 4 hrs. | 6 hrs. |
|---|---|---|---|---|
| Example 10 | 100 | 100 | 100 | 70 |
| Example 11 | 100 | 100 | 100 | 100 |
| Example 12 | 100 | 100 | 100 | 100 |
| Example 13 | 96 | 92 | 96 | 94 |
| Comparative Example 6 | 100 | 78 | 68 | 40 |

Unit: %

EXAMPLE 14 AND COMPARATIVE EXAMPLE 7 (Repellent lotion)

The 2-hydroxymethyl-menthol (HMMO) obtained in the foregoing Synthesizing Example 14 was formulated according to the recipe shown in Table 9 below to prepare a repellent lotion of Example 14.

TABLE 9

|  | Example 14 | Comparative Example 7 |
|---|---|---|
| 95° non-denatured alcohol | 87 | 87 |
| Pure water | 10 | 10 |
| N,N-diethyltoluamide | — | 3 |
| HMMO | 3 | — |

Unit: wt. %

The noxious-insect repellency test against tiger mosquito imagoes was conducted with the repellent lotions, and Example 14 was compared with Comparative Example 7. The results are shown in Table 10. As evident from Table 10, the repellent lotion of the present invention formulated with HMMO exhibited an excellent noxious-insect repelling effect and durability.

TABLE 10

| After application | 30 min. | 1 hr. | 4 hrs. | 6 hrs. |
|---|---|---|---|---|
| Example 14 | 100 | 100 | 100 | 100 |
| Comparative Example 7 | 100 | 78 | 68 | 40 |

Unit: %

EXAMPLES 15–18, AND COMPARATIVE EXAMPLES 8 (Repellent lotion)

The 2-hydroxymethyl-4-(t-butyl)-cyclohexanol, 2-hydroxymethyl-cyclooctanol, 2-hydroxymethyl-4-ethyl-cyclopentanol and 2-hydroxymethyl-4-isopropyl-6-methyl-cyclohexanol obtained in the foregoing Synthesizing Examples 15–17 and 19, respectively, were formulated according to the recipe shown in Table 11 below to prepare repellent lotions of Examples 15–18, and the noxious-insect repellency test was conducted.

TABLE 11

| | Comparative Example | Example | | | |
|---|---|---|---|---|---|
| | 8 | 15 | 16 | 17 | 18 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-Hydroxymethyl-4-(t-butyl)-cyclohexanol | — | 3 | — | — | — |
| 2-Hydroxymethyl-cyclooctanol | — | — | 3 | — | — |
| 2-Hydroxymethyl-4-ethyl-cyclopentanol | — | — | — | 3 | — |
| 2-Hydroxymethyl-4-isopropyl-6-methyl-cyclohexanol | — | — | — | — | 3 |

Unit: wt. %

The noxious-insect repellency test against tiger mosquito imagoes was conducted with the above repellent lotions, and Examples 15–18 were compared with Comparative Example 8. The results are shown in Table 12. As evident from Table 12, the repellent lotions of the present invention formulated with 2-hydroxymethyl-2-ethyl-cyclopentanol, 2-hydroxymethyl-4-(t-butyl)-cyclohexanol, 2-hydroxymethyl-cylooctanol, 2-hydroxymethyl-4-ethyl-cyclopentanol and 2-hydroxymethyl-4-isopropyl-6-methyl-cyclohexanol, respectively, exhibited an excellent noxious-insect repelling effect and durability.

TABLE 12

| After application | 30 min. | 1 hr. | 4 hrs. | 6 hrs. |
|---|---|---|---|---|
| Comparative Example 8 | 100 | 78 | 68 | 40 |
| Example 15 | 100 | 100 | 100 | 86 |
| Example 16 | 100 | 100 | 100 | 100 |
| Example 17 | 100 | 100 | 86 | 74 |
| Example 18 | 100 | 100 | 100 | 100 |

Unit: %

EXAMPLE 19 AND COMPARATIVE EXAMPLE 9 (Repellent lotion)

The 2-hydroxymethyl-menthone (HMMT) obtained in the foregoing Synthesizing Example 24 was formulated according to the recipe shown in Table 13 below to prepare the repellent lotion of the present invention. The 2-ethyl-1,3-hexanediol formulated in Comparative Example 9 is a known compound which is said to have an excellent repelling effect.

TABLE 13

| Synthetic component | Example 19 | Comparative Example 9 |
|---|---|---|
| 95° non-denatured alcohol | 87 | 87 |
| Pure water | 10 | 10 |
| 2-Ethyl-1,3-hexanediol | — | 3 |
| HMMT | 3 | — |

Unit: wt. %

The noxious-insect repellency test against tiger mosquito imagoes was conducted with these repellent lotions, and Example 19 was compared with Comparative Example 9. The results are shown in Table 14. As evident from Table 14, the repellent lotion of the present invention formulated with HMMT exhibited an excellent noxious-insect repelling effect and durability.

TABLE 14

| After application | 30 min. | 1 hr. | 4 hrs. | 6 hrs. |
|---|---|---|---|---|
| Example 19 | 100 | 100 | 100 | 95 |
| Comparative Example 9 | 95 | 85 | 70 | 20 |

Unit: %

EXAMPLES 20–23 AND COMPARATIVE EXAMPLE 10 (Repellent lotion)

The repellent lotions of Examples 20–23 and Comparative Example 10 were prepared according to the recipe shown in Table 15 and the noxious-insect repellency test was conducted.

TABLE 15

| | Comparative Example | Example | | | |
|---|---|---|---|---|---|
| Synthetic component | 10 | 20 | 21 | 22 | 23 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-(1-Hydroxyethyl)-4-methyl-cyclohexanol | — | 3 | — | — | — |
| 2-(1-Hydroxyethyl)-cyclooctanol | — | — | 3 | — | 1 |
| 2-(1-Hydroxybutyl)-3-ethyl-cyclopentanol | — | — | — | 3 | 1 |
| 2-(1-Hydroxyethyl)-cyclodecanol | — | — | — | — | 1 |

Unit: wt. %

The noxious-insect repellency test against tiger mosquito imagoes was conducted with the repellent lotions of Examples 20–23 and Comparative Example 10, and these examples were compared with each other. The results are shown in Table 16.

TABLE 16

| After application | 30 min. | 1 hr. | 4 hrs. | 6 hrs. |
|---|---|---|---|---|
| Comparative Example 10 | 100 | 78 | 68 | 40 |
| Example 20 | 100 | 100 | 100 | 96 |
| Example 21 | 100 | 100 | 84 | 78 |
| Example 22 | 100 | 100 | 100 | 100 |
| Example 23 | 100 | 100 | 100 | 100 |

Unit: %

As evident from Table 16, the repellent lotions of the present invention containing 2-(1-hydroxyethyl)-4-methyl-cyclohexanol, 2-(1-hydroxyethyl)-cyclooctanol, 2-(1-hydroxybutyl)-3-ethyl-cyclopentanol and 2-(1-hydroxyethyl)-cyclodecanol 4-methyl-cyclohexanol, respectively, exhibited an excellent noxious-insect repelling effect and durability.

EXAMPLES 24–26 AND COMPARATIVE EXAMPLE 11 (Milky lotion)

The milky lotions of Examples 24–26 and Comparative Example 11 were prepared according to the recipe shown in Table 17 and the noxious-insect repellency test was conducted.

TABLE 17

|  | Comparative Example | Example | | |
|---|---|---|---|---|
|  | 11 | 24 | 25 | 26 |
| Vaseline | 2.0 | 2.0 | 2.0 | 2.0 |
| Cetanol | 1.0 | 1.0 | 1.0 | 1.0 |
| 1,3-Butylene glycol | 6.0 | 6.0 | 6.0 | 6.0 |
| Sodium N-acylglutamate | 1.0 | 1.0 | 1.0 | 1.0 |
| Carboxyvinyl polymer | 0.2 | 0.2 | 0.2 | 0.2 |
| N,N-diethyltoluamide | 5.0 | — | — | — |
| 2-(1-Hydroxypropyl)-4-methyl-cyclohexanol | — | 5.0 | — | — |
| 2-(1-Hydroxyethyl)-cycloheptanol | — | — | 5.0 | — |
| 2-(1-Hydroxyethyl)-3,4-dimethyl-cyclohexanol | — | — | — | 5.0 |
| Pure water | Balance | Balance | Balance | Balance |

Unit wt. %

The noxious-insect repellency test against tiger mosquito imagoes was conducted with the milky lotions of Examples 24–26 and Comparative Example 11, and these examples were compared with each other. The results are shown in Table 18.

TABLE 18

| After application | 30 min. | 1 hr. | 4 hrs. | 6 hrs. |
|---|---|---|---|---|
| Comparative Example 11 | 100 | 100 | 74 | 52 |
| Example 24 | 100 | 100 | 100 | 100 |
| Example 25 | 100 | 100 | 100 | 68 |
| Example 26 | 100 | 100 | 100 | 100 |

Unit: %

As evident from Table 18, the milky lotions of the present invention containing 2-(1-hydroxypropyl)-4-methyl-cyclohexanol, 2-(1-hydroxyethyl)-cycloheptanol and 2-(1-hydroxyethyl)-3,4-dimethyl-cyclohexanol, respectively, exhibited an excellent noxious-insect repelling effect and durability.

EXAMPLES 27–32 AND COMPARATIVE EXAMPLE 12 (Repellent lotion)

The 3-(1-hydroxypropyl)-borneol, 3-(1-hydroxyethyl)-borneol, 3-(1-hydroxybutyl)-borneol and 3-(1-hydroxy-2-methylpropyl)-borneol obtained by the foregoing Synthesizing Examples 20–23, respectively, were formulated according to the recipe shown in Table 19 below to prepare the repellent lotions of Examples 27–32 of the present invention. The noxious-insect repellency test was conducted.

TABLE 19

|  | Comparative Example | Example | | | | | |
|---|---|---|---|---|---|---|---|
|  | 12 | 27 | 28 | 29 | 30 | 31 | 32 |
| 95° non-denatured alcohol | 87 | 87 | 87 | 87 | 87 | 87 | 87 |
| Pure water | 10 | 10 | 10 | 10 | 10 | 10 | 10 |
| N,N-diethyltoluamide | 3 | — | — | — | — | — | — |
| 3-(1-Hydroxymethyl)-borneol | — | 3 | — | — | — | 2 | — |
| 3-(1-Hydroxyethyl)-borneol | — | — | 3 | — | — | 1 | 1.5 |
| 3-(1-Hydroxybutyl)-borneol | — | — | — | 3 | — | — | 1.5 |
| 3-(1-Hydroxy-2-methylpropyl)-borneol | — | — | — | — | 3 | — | — |

Unit: wt. %

The noxious-insect repellency test against tiger mosquito imagoes was conducted with these repellent lotions, and Examples 27–32 were compared with Comparative Example 12. The results are shown in Table 20.

TABLE 20

| After application | 30 min. | 1 hr. | 4 hrs. | 6 hrs. |
|---|---|---|---|---|
| Comparative Example 11 | 100 | 100 | 68 | 40 |
| Example 27 | 100 | 100 | 100 | 95 |
| Example 28 | 100 | 100 | 100 | 93 |
| Example 29 | 100 | 100 | 97 | 90 |
| Example 30 | 100 | 100 | 95 | 89 |
| Example 31 | 100 | 100 | 100 | 95 |
| Example 32 | 100 | 100 | 99 | 92 |

Unit: %

As evident from Table 20, the repellent lotions of the present invention containing 3-(1-hydroxypropyl)-borneol, 3-(1-hydroxyethyl)-borneol, 3-(1-hydroxybutyl)-borneol and 3-(1-hydroxy-2-methylpropyl)-borneol, respectively, exhibited an excellent noxious-insect repelling effect and durability.

EXAMPLES 33–36 AND COMPARATIVE EXAMPLE 13 (Milky lotion)

The 3-(1-hydroxyethyl)-borneol, 3-(1-hydroxypropyl)-borneol and 3-(1-hydroxybutyl)-borneol obtained in the foregoing Synthesizing Examples 20, 21 and 23, respectively, were formulated according to the recipe shown in Table 21 below to prepare the milky lotions of Examples 33–36. The noxious-insect repellency test was conducted.

TABLE 21

|  | Comparative Example | Example | | | |
|---|---|---|---|---|---|
| Synthetic component | 13 | 33 | 34 | 35 | 36 |
| Vaseline | 2.0 | 2.0 | 2.0 | 2.0 | 2.0 |
| Cetanol | 1.0 | 1.0 | 1.0 | 1.0 | 1.0 |
| 1,3-Butylene glycol | 6.0 | 6.0 | 6.0 | 6.0 | 6.0 |
| Sodium N-acylglutamate | 1.0 | 1.0 | 1.0 | 1.0 | 1.0 |
| Carboxyvinyl polymer | 0.2 | 0.2 | 0.2 | 0.2 | 0.2 |
| N,N-diethyltoluamide | 5.0 | — | — | — | — |
| 3-(1-Hydroxyethyl)-borneol | — | 5.0 | — | — | 3.0 |

TABLE 21-continued

| Synthetic component | Comparative Example 13 | Example 33 | Example 34 | Example 35 | Example 36 |
|---|---|---|---|---|---|
| 3-(1-Hydroxypropyl)-borneol | — | — | 5.0 | — | 2.0 |
| 3-(1-Hydroxybutyl)-borneol | — | — | — | 5.0 | — |
| Pure water | Balance | Balance | Balance | Balance | Balance |

Unit: wt. %

The noxious-insect repellency test against tiger mosquito imagoes was conducted with these milky lotions, and Examples 33–36 were compared with Comparative Example 13. The results are shown in Table 22.

TABLE 22

| After application | 30 min. | 1 hr. | 4 hrs. | 6 hrs. |
|---|---|---|---|---|
| Comparative Example 13 | 100 | 100 | 74 | 52 |
| Example 33 | 100 | 100 | 100 | 99 |
| Example 34 | 100 | 100 | 100 | 93 |
| Example 35 | 100 | 100 | 100 | 91 |
| Example 36 | 100 | 100 | 100 | 93 |

Unit: %

As evident from Table 2.2, the milky lotions of the present invention containing 3-(1-hydroxyethyl)-borneol, 3-(1-hydroxypropyl)-borneol and 3-(1-hydroxybutyl)-borneol, respectively, exhibited an excellent noxious-insect repelling effect and durability.

EXAMPLES 37 AND 38, AND COMPARATIVE EXAMPLES 14 AND 15 (Repellent lotion)

The 2-(1-hydroxyisopropyl)-5-methyl-cyclopentanone obtained in the foregoing Synthesizing Example 25 was formulated according to the recipe shown in Table 23 below to prepare the repellent lotions of Examples 37 and 38. The noxious-insect repellency test was conducted.

TABLE 23

| Synthetic component | Example 37 | Example 38 | Comparative Example 14 | Comparative Example 15 |
|---|---|---|---|---|
| 95° non-denatured alcohol | 89 | 87 | 87 | 85 |
| Pure water | 10 | 10 | 10 | 10 |
| N,N-diethyltoluamide | — | — | 3 | 5 |
| Compound of Synthesizing Example 25 | 1 | 3 | — | — |

Unit: wt. %

The results of the noxious-insect repellency test are shown in Table 24. As evident from Table 24, the repellent lotions of the present invention containing 2-(1-hydroxyisopropyl)-5-methyl-cyclopentanone exhibited an excellent noxious-insect repelling effect and durability.

TABLE 24

| After application | 30 min. | 1 hr. | 4 hrs. | 6 hrs. |
|---|---|---|---|---|
| Example 37 | 100 | 100 | 83 | 72 |
| Example 38 | 100 | 100 | 89 | 80 |
| Comparative Example 14 | 100 | 78 | 68 | 40 |
| Comparative Example 15 | 100 | 85 | 70 | 55 |

Unit: %

EXAMPLES 39–43 AND COMPARATIVE EXAMPLES 16 AND 17 (Repellent lotion)

The 8-hydroxy-2-methyl-p-menthan-3-one, 8-hydroxy-2-methylene-p-menthan-3-one, 8-hydroxy-2-ethyl-p-menthan-3-one, 8-hydroxy-2-propenyl-p-menthan-1-one and 8-hydroxy-2-hexyl-p-menthan-3-one obtained in the foregoing Synthesizing Examples 26–30, respectively, were formulated according to the recipe shown in Table 25 below to prepare the repellent lotions of Examples 39–43. The noxious-insect repellency test was conducted.

TABLE 25

| Synthetic component | Example 39 | Example 40 | Example 41 | Example 42 | Example 43 | Comparative Example 16 | Comparative Example 17 |
|---|---|---|---|---|---|---|---|
| 95° non-denatured alcohol | 87 | 87 | 87 | 87 | 87 | 87 | 87 |
| Pure water | 10 | 10 | 10 | 10 | 10 | 10 | 10 |
| N,N-diethyltoluamide | — | — | — | — | — | 3 | — |
| p-Menthane-3,8-diol | — | — | — | — | — | — | 3 |
| Compound of Synthesizing Example 26 | 3 | — | — | — | — | — | — |
| Compound of Synthesizing Example 27 | — | 3 | — | — | — | — | — |
| Compound of Synthesizing Example 28 | — | — | 3 | — | — | — | — |
| Compound of Synthesizing Example 29 | — | — | — | 3 | — | — | — |
| Compound of Synthesizing Example 30 | — | — | — | — | 3 | — | — |

Unit: wt. %

The results of the noxious-insect repellency test are shown in Table 26. As evident from Table 26, the repellent lotions of the present invention containing the 8-hydroxy-p-menthan-3-one derivative of the present invention exhibited an excellent noxious-insect repelling effect and durability.

TABLE 26

| After application | 30 min. | 1 hr. | 4 hrs. | 6 hrs. |
|---|---|---|---|---|
| Example 39 | 100 | 100 | 93 | 88 |
| Example 40 | 100 | 100 | 95 | 91 |
| Example 41 | 100 | 100 | 100 | 98 |
| Example 42 | 100 | 100 | 100 | 97 |
| Example 43 | 100 | 98 | 93 | 87 |
| Comparative Example 16 | 100 | 78 | 68 | 40 |
| Comparative Example 17 | 100 | 100 | 75 | 55 |

Unit: %

EXAMPLES 44–47 AND COMPARATIVE EXAMPLE 18 (Repellent lotion)

The repellent lotions of Examples 44–47 and Comparative Example 18 were prepared according to the recipe shown in Table 27 and the noxious-insect repellency test was conducted.

TABLE 27

| Synthetic component | Comparative Example | Example | | | |
|---|---|---|---|---|---|
| | 18 | 44 | 45 | 46 | 47 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-Hydroxymethyl-4-(t-butyl)-cyclohexanone | — | 3 | — | — | 1 |
| 2-Hydroxymethyl-cyclooctanone | — | — | 3 | — | — |
| 2-Hydroxymethyl-4-ethyl-cyclopentane | — | — | — | 3 | — |
| 2-Hydroxymethyl-4-isopropyl-6-methyl-cyclohexanone | — | — | — | — | 2 |

Unit: wt. %

The noxious-insect repellency test against tiger mosquito imagoes was conducted with the repellent lotions of Examples 44–47 and Comparative Example 17, and compared with each other. The results are shown in Table 28.

TABLE 28

| After application | 30 min. | 1 hr. | 4 hrs. | 6 hrs. |
|---|---|---|---|---|
| Comparative Example 18 | 100 | 78 | 68 | 40 |
| Example 44 | 100 | 94 | 94 | 88 |
| Example 45 | 100 | 100 | 100 | 94 |
| Example 46 | 100 | 100 | 86 | 74 |
| Example 47 | 100 | 100 | 100 | 100 |

Unit: %

As evident from Table 28, the repellent lotions of the present invention containing 2-hydroxymethyl-4-(t-butyl)-cyclohexanone, 2-hydroxymethyl-cyclooctanone, 2-hydroxymethyl-4-ethyl-cyclopentanone and 2-hydroxymethyl-4-isopropyl-6-methyl-cyclohexanone, respectively, exhibited an excellent noxious-insect repelling effect and durability.

EXAMPLES 48–50 AND COMPARATIVE EXAMPLE 19 (Milky lotion)

The milky lotions of Examples 48–50 and Comparative Example 19 were prepared according to the recipe shown in Table 29 and the noxious-insect repellency test was conducted.

TABLE 29

| Synthetic component | Comparative Example | Example | | |
|---|---|---|---|---|
| | 19 | 48 | 49 | 50 |
| Vaseline | 2.0 | 2.0 | 2.0 | 2.0 |
| Cetanol | 1.0 | 1.0 | 1.0 | 1.0 |
| 1,3-Butylene glycol | 6.0 | 6.0 | 6.0 | 6.0 |
| Sodium N-acylglutamate | 1.0 | 1.0 | 1.0 | 1.0 |
| Carboxyvinyl polymer | 0.2 | 0.2 | 0.2 | 0.2 |
| N,N-diethyltoluamide | 5.0 | — | — | — |
| 2-Hydroxymethyl-4-methyl-cyclohexanone | — | 5.0 | — | 1.0 |
| 2-Hydroxymethyl-3,4-dimethyl-cyclohexanone | — | — | 5.0 | 1.0 |
| 2-Hydroxymethyl-cyclododecanone | — | — | — | 3.0 |
| Pure water | Balance | Balance | Balance | Balance |

Unit: wt. %

The noxious-insect repellency test against tiger mosquito imagoes was conducted with the milky lotions of Examples 48–50 and Comparative Example 19, and these examples were compared with each other. The results are shown in Table 30.

TABLE 30

| After application | 30 min. | 1 hr. | 4 hrs. | 6 hrs. |
|---|---|---|---|---|
| Comparative Example 19 | 100 | 100 | 74 | 52 |
| Example 48 | 100 | 100 | 94 | 86 |
| Example 49 | 100 | 100 | 96 | 84 |
| Example 50 | 100 | 96 | 86 | 74 |

Unit: %

As evident from Table 30, the milky lotions of the present invention containing 2-hydroxymethyl-4-methyl-cyclohexanone, 2-hydroxymethyl-3,4-dimethyl-cyclohexanone and 2-hydroxymethyl-cyclododecanone, respectively, exhibited an excellent noxious-insect repelling effect and durability.

EXAMPLES 51–54 AND COMPARATIVE EXAMPLE 20 (Repellent lotion)

The repellent lotions of Examples 51–54 and Comparative Example 20 were prepared according to the recipe shown in Table 31 and the noxious-insect repellency test was conducted.

TABLE 31

| Synthetic component | Comparative Example | Example | | | |
|---|---|---|---|---|---|
| | 20 | 51 | 52 | 53 | 54 |
| 95° non-denatured alcohol | 87 | 87 | 87 | 87 | 87 |
| Pure water | 10 | 10 | 10 | 10 | 10 |
| N,N-diethyltoluamide | 3 | — | — | — | — |
| 2-(1-Hydroxyethyl-4-methyl-cyclohexanone | — | 3 | — | — | — |
| 2-(1-Hydroxyethyl)-cyclooctaneone | — | — | 3 | — | — |
| 2-(1-Hydroxybutyl)-3-ethyl-cyclopentanone | — | — | — | 3 | — |
| 2-(1-Hydroxyethyl-)-cyclodecanone | — | — | — | — | 2 |

Unit: wt. %

The noxious-insect repellency tests against tiger mosquito imagoes were conducted with the repellent lotions of Examples 51–54 and Comparative Example 20, and compared with each other. The results are shown in Table 32.

TABLE 32

| After application | 30 min. | 1 hr. | 4 hrs. | 6 hrs. |
|---|---|---|---|---|
| Comparative Example 20 | 100 | 100 | 68 | 40 |
| Example 51 | 100 | 100 | 94 | 82 |
| Example 52 | 100 | 100 | 100 | 100 |
| Example 53 | 100 | 100 | 98 | 86 |
| Example 54 | 100 | 100 | 100 | 100 |

Unit: %

As evident from Table 32, the repellent lotions of the present invention containing 2-(1-hydroxyethyl)-4-methyl-cyclohexanone, 2-(1-hydroxyethyl)-cyclooctanone, 2-(1-hydroxybutyl)-3-ethyl-cyclopentanone and 2-(1-hydroxyethyl)-cyclododecanone, respectively, exhibited an excellent noxious-insect repelling effect and durability.

EXAMPLES 55–57 AND COMPARATIVE EXAMPLE 21 (Milky lotion)

The milky lotions of Examples 55–57 and Comparative Example 21 were prepared according to the recipe shown in Table 33 and the noxious-insect repellency test was conducted.

TABLE 33

| Synthetic component | Comparative Example 21 | Example 55 | Example 56 | Example 57 |
|---|---|---|---|---|
| Vaseline | 2.0 | 2.0 | 2.0 | 2.0 |
| Cetanol | 1.0 | 1.0 | 1.0 | 1.0 |
| 1,3-Butylene glycol | 6.0 | 6.0 | 6.0 | 6.0 |
| Sodium N-acylglutamate | 1.0 | 1.0 | 1.0 | 1.0 |
| Carboxyvinyl polymer | 0.2 | 0.2 | 0.2 | 0.2 |
| N,N-diethyltoluamide | 5.0 | — | — | — |
| 2-(1-Hydroxyamyl)4-methyl-cyclohexanone | — | 5.0 | — | — |
| 2-(1-Hydroxyethyl)-cycloheptanone | — | — | 5.0 | 1.0 |
| 2-(1-Hydroxyethyl)-3,4-dimethyl-cyclohexanone | — | — | — | 4.0 |
| Pure water | Balance | Balance | Balance | Balance |

Unit: wt. %

The noxious-insect repellency test against tiger mosquito imagoes was conducted with the milky lotions of Examples 55–57 and Comparative Example 21, and these examples were compared with each other. The results are shown in Table 34.

TABLE 34

| After application | 30 min. | 1 hr. | 4 hrs. | 6 hrs. |
|---|---|---|---|---|
| Comparative Example 21 | 100 | 100 | 74 | 52 |
| Example 55 | 100 | 100 | 100 | 84 |
| Example 56 | 100 | 100 | 100 | 90 |
| Example 57 | 100 | 100 | 100 | 96 |

Unit: %

As evident from Table 34, the milky lotions of the present invention containing 2-(1-hydroxyamyl)-4-methyl-cyclohexanone, 2-(1-hydroxyethyl)-cycloheptanone and 2-(1-hydroxyethyl)-3,4-dimethyl-cyclohexanone, respectively, exhibited an excellent noxious-insect repelling effect and durability.

EXAMPLES 58–63 AND COMPARATIVE EXAMPLE 22 (Repellent lotion)

The 3-(1-hydroxymethyl)-camphor, 3-(1-hydroxyethyl)-camphor, 3-(1-hydroxybutyl)-camphor and 3-(1-hydroxy-2-methylpropyl)-camphor obtained in the foregoing Synthesizing Examples 31–34, respectively, were formulated according to the recipe shown in Table 35 below to prepare the repellent lotions of Examples 58–63 and Comparative Example 22. The noxious-insect repellency test was conducted.

TABLE 35

| Synthetic component | Comparative Example 22 | Example 58 | Example 59 | Example 60 | Example 61 | Example 62 | Example 63 |
|---|---|---|---|---|---|---|---|
| 95° non-denatured alcohol | 87 | 87 | 87 | 87 | 87 | 87 | 87 |
| Pure water | 10 | 10 | 10 | 10 | 10 | 10 | 10 |
| N,N-diethyltoluamide | 3 | — | — | — | — | — | — |
| 3-(1-Hydroxymethyl)-camphor | — | 3 | — | — | — | 2 | — |
| 3-(1-Hydroxyethyl)-camphor | — | — | 3 | — | — | 1 | 1.5 |
| 3-(1-Hydroxybutyl)-camphor | — | — | — | 3 | — | — | 1.5 |
| 3-(1-Hydroxy-2-methylpropyl)-camphor | — | — | — | — | 3 | — | — |

Unit: wt. %

The noxious-insect repellency test against tiger mosquito imagoes was conducted with the repellent lotions of Examples 58–63 and Comparative Example 22, and these examples were compared with each other. The results are shown in Table 36.

TABLE 36

| After application | 30 min. | 1 hr. | 4 hrs. | 6 hrs. |
|---|---|---|---|---|
| Comparative Example 22 | 100 | 100 | 68 | 40 |
| Example 58 | 100 | 100 | 99 | 96 |
| Example 59 | 100 | 100 | 100 | 97 |
| Example 60 | 100 | 100 | 100 | 100 |
| Example 61 | 100 | 100 | 100 | 100 |
| Example 62 | 100 | 100 | 100 | 97 |
| Example 63 | 100 | 100 | 100 | 99 |

Unit: %

As evident from Table 36, the repellent lotions of the present invention containing 3-(1-hydroxymethyl)-camphor, 3-(1-hydroxyethyl)-camphor, 3-(1-hydroxybutyl)-camphor and 3-(1-hydroxy-2-methylpropyl)-camphor, respectively, exhibited an excellent noxious-insect repelling effect and durability.

EXAMPLES 64–67 AND COMPARATIVE EXAMPLE 23 (Milky lotion)

The milky lotions of Examples 64–67 and Comparative Example 23 were prepared according to the recipe shown in Table 37 and the noxious-insect repellency test was conducted.

TABLE 37

| Synthetic component | Comparative Example 23 | Example 64 | Example 65 | Example 66 | Example 67 |
|---|---|---|---|---|---|
| Vaseline | 2.0 | 2.0 | 2.0 | 2.0 | 2.0 |
| Cetanol | | | | | |
| 1,3-Butylene glycol | 6.0 | 6.0 | 6.0 | 6.0 | 6.0 |
| Sodium N-acylglutamate | 1.0 | 1.0 | 1.0 | 1.0 | 1.0 |
| Carboxyvinyl polymer | 0.2 | 0.2 | 0.2 | 0.2 | 0.2 |
| N,N-diethyltoluamide | 5.0 | — | — | — | — |
| 3-(1-Hydroxymethyl)-camphor | — | 5.0 | — | — | 3.0 |
| 3-(1-Hydroxyethyl)-camphor | — | — | 5.0 | 2.0 | 2.0 |
| 3-(1-Hydroxybuthyl)-camphor | — | — | — | 5.0 | — |
| Pure water | Balance | Balance | Balance | Balance | Balance |

Unit: wt. %

The noxious-insect repellency tests against tiger mosquito imagoes were conducted with the milky lotions of Examples 64–67 and Comparative Example 23, and compared with each others. The results are shown in Table 38.

TABLE 38

| After application | 30 min. | 1 hr. | 4 hrs. | 6 hrs. |
|---|---|---|---|---|
| Comparative Example 23 | 100 | 100 | 74 | 52 |
| Example 64 | 100 | 100 | 100 | 84 |
| Example 65 | 100 | 100 | 100 | 100 |
| Example 66 | 100 | 100 | 100 | 100 |
| Example 67 | 100 | 100 | 100 | 91 |

Unit: %

As evident from Table 38, the milky lotions of the present invention containing 3-(1-hydroxyethyl)-camphor, 3-(1-hydroxypropyl)-camphor and 3-(1-hydroxybutyl)-camphor, respectively, exhibited an excellent noxious-insect repelling effect and durability.

EXAMPLES 68–72 AND COMPARATIVE EXAMPLE 24 (Repellent lotion)

2-Hydroxymethyl-cyclohexanol and 2-hydroxymethyl-2-alkyl-cyclohexanol derivatives having straight chain saturated hydrocarbon radicals having 2, 4, 6, 8 and 14 carbon atoms, respectively, substituting at the second carbon atom of the cyclohexane ring were synthesized in the same procedure as Synthesizing Example 6. Then, these compounds were dissolved in a 40 wt. % ethanol aqueous solution to prepare the repellent lotions Examples 68–72 and Comparative Example 24. The repellent lotions of Examples 68–72 contained 2-hydroxymethyl-cyclohexanol and the above 2-hydroxymethyl-2-($C_{2-8}$-alkyl)-cyclohexanol, respectively, and the repellent lotion of Comparative Example 24 contained the above 2-hydroxymethyl-2-tetradecyl($C_{14}$-alkyl)-cyclohexanol, in an amount of 1% by weight. The noxious-insect repellency test was conducted with these repellent lotions. The results (the initial activity and the durability of the repelling effect) are shown in Table 39. From these results, it was found that the compounds having a substituent alkyl group of 8 or less carbon atoms exhibited a strong initial activity and the compounds having a substituent alkyl group of 14 or more carbon atoms did not show the repelling effect. Thus, it was demonstrated that the repelling effect depends upon the chain length of the substituent alkyl group.

TABLE 39

| After application | 30 min. | 1 hr. | 2 hrs. | 3 hrs. |
|---|---|---|---|---|
| Example 68 | 100 | 96 | 52 | 32 |
| Example 69 | 100 | 100 | 100 | 88 |
| Example 70 | 98 | 100 | 96 | 98 |
| Example 71 | 94 | 92 | 96 | 94 |
| Example 72 | 88 | 86 | 88 | 90 |
| Comparative Example 24 | 10 | 12 | 14 | 10 |

Unit: %

EXAMPLES 73–75 AND COMPARATIVE EXAMPLE 25 (Repellent lotion)

2-Hydroxymethyl-2-ethyl-cycloalkanol derivatives comprising 5, 8, 12 and 15-membered cycloalkane, respectively, were synthesized in the same procedure as Synthesizing Example 7. Then, these compounds were dissolved in a 40 wt. % ethanol aqueous solution to prepare the repellent lotions of Examples 73–75 and Comparative Example 25. The repellent lotions of Examples 73–75 contained the above cycloalkanol derivatives comprising 5–12-membered cycloalkane, respectively, and Comparative Example 25 contained the above cycloalkanol derivative comprising 15-membered cycloalkane, in an amount of 1% by weight.

The noxious-insect repellency test was conducted with these repellent lotions. The results (the initial activity and the durability of the repelling effect) are shown in Table 40. From these results, it was found that the repelling effect depends upon the ring-member carbon atom number. Namely, it has been demonstrated that when the ring-member carbon atom number is 12 or less, a strong repelling effect is exhibited and when the ring-member carbon atom number is 15 or more, the repelling effect is not exhibited.

TABLE 40

| After application | 30 min. | 1 hr. | 2 hrs. | 3 hrs. |
|---|---|---|---|---|
| Example 73 | 100 | 88 | 42 | 26 |
| Example 74 | 100 | 100 | 100 | 94 |
| Example 75 | 86 | 84 | 86 | 88 |
| Comparative Example 25 | 14 | 12 | 26 | 20 |

Unit: %

COMPARATIVE EXAMPLE 26 (Repellent lotion)

The repellent lotion of Comparative Example 26 was prepared which contained 1% by weight of 3-(1-hydroxyhexyl)-camphor synthesized according to Synthesizing Examples 31–34. With respect to the noxious-insect repelling effect, a comparative test was conducted with the repellent lotions of Comparative Example 26 and Examples 58, 59 and 61. The results are shown in Table 41. From the results, it has been found that the derivative having a hydroxyhexyl group does not exhibit the repelling effect and that the chain length of the alkyl group is significant for the repelling effect (the initial activity and the durability of the effect).

TABLE 41

| After application | 30 min. | 1 hr. | 2 hrs. | 3 hrs. |
|---|---|---|---|---|
| Example 58 | 100 | 100 | 98 | 78 |
| Example 59 | 100 | 100 | 100 | 88 |
| Example 61 | 96 | 100 | 98 | 100 |
| Comparative Example 26 | 16 | 16 | 14 | 16 |

Unit: %

EXAMPLE 76

With the purpose of investigating the properties of the compounds to be used for the present invention, solubilities in a 90 wt. % ethanol aqueous solution and stabilities at 0° C., room temperature and 40° C., of hydroxymethyl-menthol, 2-hydroxymethyl-2-butyl-cyclopentanol and 2-(1-hydroxyisopropyl)-5,6-dimethyl-cyclohexanone, were investigated. The method of assessment is shown in Table 42. Besides, the results of the investigation are shown in Tables 43–45. As shown in Table 43, when the noxious-insect repellent composition contains a repellent compound in an amount of at least 90% by weight, it has been found that the stability of the lotion is questioned. Furthermore, it can be understood that the quantity of the repellent compound is preferred to be at most 20% by weight, in view of touch in use.

TABLE 42

| Method of assessment | | |
|---|---|---|
| Solubility | Stability | Result of assessment |
| Soluble | Stable | ○ |
| Insoluble | Precipitated | X |

TABLE 43

| | | Hydroxymethyl-menthol content (wt. %) | | | | |
|---|---|---|---|---|---|---|
| | | 10% | 20% | 50% | 90% | 95% |
| 0° C. | Solubility | ○ | ○ | ○ | ○ | ○ |
| | Stability | ○ | ○ | ○ | X | X |
| Room temperature | Solubility | ○ | ○ | ○ | ○ | ○ |
| | Stability | ○ | ○ | ○ | ○ | X |
| 40° C. | Solubility | ○ | ○ | ○ | ○ | ○ |
| | Stability | ○ | ○ | ○ | ○ | ○ |

TABLE 44

| | | 2-Hydroxymethyl-2-butyl-cyclopentanol content (wt. %) | | | | |
|---|---|---|---|---|---|---|
| | | 10% | 20% | 50% | 90% | 95% |
| 0° C. | Solubility | ○ | ○ | ○ | ○ | ○ |
| | Stability | ○ | ○ | ○ | ○ | X |
| Room temperture | Solubility | ○ | ○ | ○ | ○ | ○ |
| | Stability | ○ | ○ | ○ | ○ | X |
| 40° C. | Solubility | ○ | ○ | ○ | ○ | ○ |
| | Stability | ○ | ○ | ○ | ○ | ○ |

TABLE 45

| | | 2-(1-Hydroxyisopropyl)-5,6-dimethyl-cyclohexanone content (wt. %) | | | | |
|---|---|---|---|---|---|---|
| | | 10% | 20% | 50% | 90% | 95% |
| 0° C. | Solubility | ○ | ○ | ○ | ○ | ○ |
| | Stability | ○ | ○ | ○ | ○ | X |
| Room temperature | Solubility | ○ | ○ | ○ | ○ | ○ |
| | Stability | ○ | ○ | ○ | ○ | X |
| 40° C. | Solubility | ○ | ○ | ○ | ○ | ○ |
| | Stability | ○ | ○ | ○ | ○ | ○ |

EXAMPLE 77

With the purpose of finding the lower limit of the content, hydroxymethyl-menthol, 2-hydroxymethyl-2-butyl-cyclopentanol and 2-(1-hydroxyisopropyl)-5,6-dimethyl-30 cyclohexanone were dissolved in a 40 wt. % ethanol aqueous solution, respectively. An hour after application, the noxious-insect repellency test was conducted. The percent repellencies are shown in Table 46. From these results, it has been found that the content of at least 0.1%, preferably at least 3%, by weight, of the repellent compound is required for achieving the initial activity and the durability of the effect.

TABLE 46

| Content (wt. %) | 0.05% | 0.1% | 1% | 3% |
|---|---|---|---|---|
| Hydroxymethyl-menthol | 18 | 48 | 78 | 92 |
| 2-Hydroxymethyl-2-butyl-cyclopentanol | X | 24 | 60 | 88 |
| 2-(1-Hydroxyisopropyl)-5,6-dimethyl-cyclohexanone | X | 30 | 70 | 94 |

(X: no repelling effect was found)

INDUSTRIAL APPLICABILITY

As explained above, the noxious-insect repellents according to the present invention exhibit an excellent noxious-insect repelling effect and durability. Besides, since they are substantially odorless, the noxious-insect repellents of the present invention do not give the users unpleasant feelings. Furthermore, the repellents of the invention, since they repel noxious-insects such as mosquitoes conveying pathogenic microbes, are effective for preventing malaria or other diseases, and, therefore, very useful.

What is claimed is:

1. A method of repelling noxious insects comprising the step of exposing said noxious insects to a composition containing from 0.1 to 90 wt. %, based on the total weight of the composition, of at least one of 2-(1-hydroxyalkyl)-cycloalkanols represented by at least one of the following formulae (9) and (10):

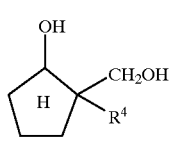

(9)

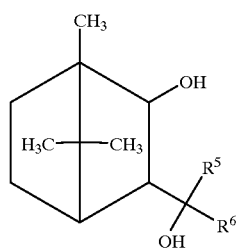

(10)

wherein R⁴ is a straight-chain or branched, saturated or unsaturated, hydrocarbon radical having 1–8 carbon atoms and R⁵ and R⁶ are hydrogens or lower alkyl groups having at most 3 carbon atoms and the sum of the carbon atoms of R⁵ and R⁶ is 0–3.

2. The method of claim 1, wherein the 2-(1-hydroxyalkyl) cycloalkanol comprises a compound of formula (9).

3. The method of claim 1, wherein the 2-(1-hydroxyalkyl) cycloalkanol comprises a compound of formula (10).

4. The method of claim 1, wherein said noxious insects are selected from the group consisting of mosquitoes, black flies, ticks, millipedes, armyworms and slugs.

5. The method of claim 1, wherein the composition is applied to a human or an animal.

6. The method of claim 4, wherein the composition is applied to a substrate.

7. The method of claim 1, wherein the noxious insects are mosquitoes.

8. Lift The method of claim 7, wherein the mosquitoes are tiger mosquitoes.

9. The method of claim 6, wherein the substrate is selected from the group consisting of a sheet, film and net.

10. The method of claim 1, wherein the 2-(1-hydroxyalkyl)cycloalkanol is contained in an amount of from 3–20% by weight.

* * * * *